United States Patent
Brefort et al.

(10) Patent No.: US 10,815,528 B2
(45) Date of Patent: Oct. 27, 2020

(54) MIRNAS AS NON-INVASIVE BIOMARKERS FOR INFLAMMATORY BOWEL DISEASE

(71) Applicant: Hummingbid Diagnostics GmbH, Heidelberg (DE)

(72) Inventors: Thomas Brefort, Ebersberg (DE); Andre Franke, Kronshagen (DE); Georg Hemmrich-Stanisak, Osterronfeld (DE); Matthias Hubenthal, Kiel (DE); Matthias Scheffler, Heidelberg (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 0 days.

(21) Appl. No.: 15/520,751

(22) PCT Filed: Jul. 23, 2015

(86) PCT No.: PCT/EP2015/066832
§ 371 (c)(1),
(2) Date: Apr. 20, 2017

(87) PCT Pub. No.: WO2016/066288
PCT Pub. Date: May 6, 2016

(65) Prior Publication Data
US 2017/0306407 A1  Oct. 26, 2017

(30) Foreign Application Priority Data

Oct. 28, 2014  (EP) .................................... 14190596
Mar. 2, 2015  (EP) .................................... 15157101

(51) Int. Cl.
*C12Q 1/6883* (2018.01)

(52) U.S. Cl.
CPC ..... *C12Q 1/6883* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2013/0035251 A1* 2/2013 Keller .................. C12Q 1/6886
506/9

FOREIGN PATENT DOCUMENTS

WO  2009/120877 A2  10/2009
WO  2013/043482 A1  3/2013

OTHER PUBLICATIONS

Jones et al Clinical Cancer Research. Nov. 2013. 20(1):253-264.*
Turner et al. J Crohn's and Colitis. 2014. 8: 1464-1470 (Year: 2014).*
International Search Report in PCT/EP2015/066832, dated Aug. 10, 2015, 3 pages.
Paraskevi, et al., "Micro-RNAs as Regulators and Possible Diagnostic Bio-Markers in Inflammatory Bowel Disease," Journal of Crohn's and Colitis, Elsevier BV, NL, vol. 5, No. 6, May 21, 2011, pp. 520-524.
Wu et al., Peripheral Blood MicroRNAs Distinguish Active Ulcerative Colitis and Crohn's Disease, Inflammatory Bowel Diseases, vol. 17, No. 1, Jan. 1, 2011, pp. 241-250.

* cited by examiner

*Primary Examiner* — Carla J Myers
(74) *Attorney, Agent, or Firm* — Kilpatrick Townswend & Stockton LLP

(57) ABSTRACT

The present invention relates to a method for diagnosis of Inflammatory Bowel Disease (IBD) based on the determination of expression profiles of miRNAs representative for diagnosis of IBD compared to a reference. In addition, the present invention relates to a kit for diagnosis of IBD comprising means for determining expression profiles of miRNAs representative for IBD.

9 Claims, 11 Drawing Sheets
Specification includes a Sequence Listing.

Figure 1

| SEQ ID NO: | mirna | median g1(CD) | median g2 (UC) | qmedian | ttest adjp | AUC | limma adjp |
|---|---|---|---|---|---|---|---|
| 1 | hsa-miR-1973 | 149 | 281 | 0.53 | 5.74E-05 | 0.81 | 8.41E-05 |
| 2 | hsa-miR-621 | 155 | 335 | 0.46 | 7.85E-04 | 0.80 | 3.92E-04 |
| 3 | hsa-miR-363 | 5045 | 10707 | 0.47 | 1.89E-03 | 0.76 | 1.21E-03 |
| 4 | hsa-miR-1251 | 89 | 141 | 0.63 | 3.82E-04 | 0.77 | 2.29E-04 |
| 5 | hsa-let-7d* | 96 | 50 | 1.92 | 8.94E-04 | 0.22 | 7.36E-04 |
| 6 | hsa-miR-127-5p | 61 | 141 | 0.43 | 1.27E-03 | 0.75 | 5.96E-04 |
| 7 | hsa-miR-136 | 31 | 56 | 0.55 | 1.27E-03 | 0.74 | 1.24E-03 |
| 8 | hsa-miR-616 | 39 | 24 | 1.61 | 1.80E-03 | 0.26 | 1.84E-03 |
| 9 | hsa-miR-548d-5p | 31 | 16 | 1.92 | 1.59E-04 | 0.23 | 2.23E-04 |
| 10 | hsa-miR-527 | 73 | 149 | 0.49 | 3.32E-03 | 0.74 | 2.07E-03 |
| 11 | hsa-miR-622 | 67 | 42 | 1.60 | 4.12E-03 | 0.29 | 4.40E-03 |
| 12 | hsa-miR-522 | 26 | 19 | 1.37 | 4.72E-03 | 0.31 | 3.57E-03 |
| 13 | hsa-miR-1275 | 170 | 94 | 1.81 | 5.92E-03 | 0.25 | 4.44E-03 |
| 14 | hsa-miR-1324 | 68 | 121 | 0.56 | 7.64E-03 | 0.73 | 9.18E-03 |
| 15 | hsa-miR-556-5p | 65 | 110 | 0.59 | 7.74E-03 | 0.71 | 8.76E-03 |
| 16 | hsa-miR-29a* | 27 | 20 | 1.35 | 8.55E-03 | 0.33 | 8.64E-03 |
| 17 | hsa-miR-516b* | 40 | 27 | 1.47 | 9.65E-03 | 0.28 | 1.25E-02 |
| 18 | hsa-miR-576-3p | 33 | 26 | 1.28 | 9.88E-03 | 0.32 | 1.18E-02 |
| 19 | hsa-miR-31* | 93 | 175 | 0.53 | 1.02E-02 | 0.73 | 8.24E-03 |
| 20 | hsa-miR-620 | 38 | 26 | 1.47 | 1.07E-02 | 0.29 | 1.22E-02 |
| 21 | hsa-miR-20a* | 139 | 195 | 0.71 | 1.42E-02 | 0.68 | 2.33E-02 |
| 22 | hsa-miR-599 | 35 | 25 | 1.41 | 1.54E-02 | 0.28 | 1.80E-02 |
| 23 | hsa-miR-610 | 72 | 97 | 0.74 | 1.55E-02 | 0.69 | 1.62E-02 |
| 24 | hsa-miR-302b | 31 | 22 | 1.44 | 1.57E-02 | 0.30 | 1.65E-02 |
| 25 | hsa-miR-892a | 48 | 32 | 1.49 | 1.58E-02 | 0.26 | 1.85E-02 |
| 26 | hsa-miR-1257 | 32 | 24 | 1.36 | 1.66E-02 | 0.31 | 2.20E-02 |
| 27 | hsa-miR-208a | 51 | 84 | 0.61 | 1.70E-02 | 0.67 | 1.49E-02 |
| 28 | hsa-miR-591 | 39 | 68 | 0.58 | 1.82E-02 | 0.70 | 1.72E-02 |
| 29 | hsa-miR-500* | 157 | 201 | 0.78 | 1.83E-02 | 0.69 | 1.80E-02 |
| 30 | hsa-miR-132 | 89 | 120 | 0.74 | 2.01E-02 | 0.71 | 3.04E-02 |
| 31 | hsa-miR-10a | 32 | 51 | 0.63 | 2.42E-02 | 0.69 | 2.95E-02 |
| 32 | hsa-miR-509-3p | 33 | 23 | 1.45 | 3.07E-02 | 0.34 | 2.65E-02 |
| 33 | hsa-miR-1321 | 53 | 35 | 1.52 | 4.29E-02 | 0.33 | 3.91E-02 |
| 34 | hsa-miR-203 | 32 | 25 | 1.27 | 4.29E-02 | 0.39 | 4.26E-02 |
| 35 | hsa-miR-889 | 27 | 40 | 0.69 | 4.75E-02 | 0.65 | 4.05E-02 |
| 36 | hsa-miR-1252 | 25 | 22 | 1.11 | 4.88E-02 | 0.38 | 5.85E-02 |
| 37 | hsa-miR-1974 | 955 | 1289 | 0.74 | 5.44E-02 | 0.68 | 4.90E-02 |
| 38 | hsa-miR-186* | 67 | 84 | 0.80 | 5.81E-02 | 0.64 | 5.46E-02 |
| 39 | hsa-miR-1206 | 66 | 92 | 0.72 | 6.09E-02 | 0.59 | 6.56E-02 |
| 40 | hsa-miR-145* | 52 | 78 | 0.67 | 6.18E-02 | 0.65 | 6.11E-02 |
| 41 | hsa-miR-1258 | 24 | 20 | 1.20 | 7.28E-02 | 0.37 | 6.78E-02 |
| 42 | hsa-miR-499-3p | 64 | 47 | 1.34 | 7.76E-02 | 0.34 | 7.92E-02 |
| 43 | hsa-miR-892b | 47 | 38 | 1.22 | 7.96E-02 | 0.37 | 7.17E-02 |
| 44 | hsa-miR-29b | 711 | 1081 | 0.66 | 8.52E-02 | 0.64 | 7.11E-02 |
| 45 | hsa-miR-1978 | 31 | 23 | 1.37 | 9.63E-02 | 0.37 | 9.11E-02 |
| 46 | hsa-miR-134 | 65 | 89 | 0.73 | 1.16E-01 | 0.64 | 1.16E-01 |

Figure 1 (cont.)

| | | | | | | | |
|---|---|---|---|---|---|---|---|
| 47 | hsa-miR-593 | 32 | 26 | 1.24 | 1.37E-01 | 0.40 | 1.40E-01 |
| 48 | hsa-miR-373* | 33 | 29 | 1.13 | 1.44E-01 | 0.40 | 1.37E-01 |
| 49 | hsa-miR-887 | 90 | 127 | 0.71 | 1.60E-01 | 0.65 | 1.61E-01 |
| 50 | hsa-miR-138 | 67 | 48 | 1.38 | 1.79E-01 | 0.39 | 1.75E-01 |
| 51 | hsa-miR-139-3p | 75 | 88 | 0.86 | 1.84E-01 | 0.59 | 1.82E-01 |
| 52 | hsa-miR-199b-3p | 764 | 1092 | 0.70 | 1.99E-01 | 0.61 | 1.96E-01 |
| 53 | hsa-miR-1254 | 92 | 107 | 0.86 | 2.04E-01 | 0.58 | 2.18E-01 |
| 54 | hsa-miR-708 | 39 | 51 | 0.77 | 2.29E-01 | 0.60 | 2.32E-01 |
| 55 | hsa-miR-29c* | 31 | 29 | 1.07 | 2.50E-01 | 0.42 | 2.47E-01 |
| 56 | hsa-miR-1180 | 67 | 45 | 1.49 | 2.72E-01 | 0.40 | 2.61E-01 |
| 57 | hsa-miR-302a* | 41 | 43 | 0.96 | 2.74E-01 | 0.58 | 2.78E-01 |
| 58 | hsa-miR-626 | 32 | 40 | 0.81 | 2.77E-01 | 0.59 | 3.04E-01 |
| 59 | hsa-miR-432* | 65 | 54 | 1.20 | 2.94E-01 | 0.42 | 3.09E-01 |
| 60 | hsa-miR-1914* | 127 | 145 | 0.88 | 3.07E-01 | 0.64 | 3.44E-01 |
| 61 | hsa-miR-148b* | 39 | 53 | 0.75 | 3.15E-01 | 0.58 | 3.16E-01 |
| 62 | hsa-miR-22* | 112 | 147 | 0.76 | 3.15E-01 | 0.59 | 3.13E-01 |
| 63 | hsa-miR-1274b | 115 | 119 | 0.96 | 3.43E-01 | 0.44 | 3.73E-01 |
| 64 | hsa-miR-1323 | 241 | 273 | 0.88 | 3.46E-01 | 0.58 | 3.55E-01 |
| 65 | hsa-miR-598 | 81 | 100 | 0.81 | 3.58E-01 | 0.59 | 3.83E-01 |
| 66 | hsa-miR-532-3p | 1165 | 1060 | 1.10 | 3.96E-01 | 0.54 | 3.88E-01 |
| 67 | hsa-miR-888 | 47 | 42 | 1.10 | 4.00E-01 | 0.44 | 4.19E-01 |
| 68 | hsa-miR-342-3p | 1181 | 1326 | 0.89 | 4.08E-01 | 0.57 | 4.35E-01 |
| 69 | hsa-miR-103-2* | 74 | 58 | 1.27 | 4.56E-01 | 0.43 | 4.30E-01 |
| 70 | hsa-miR-631 | 154 | 174 | 0.89 | 4.66E-01 | 0.57 | 4.71E-01 |
| 71 | hsa-miR-1975 | 1184 | 1233 | 0.96 | 4.71E-01 | 0.57 | 4.58E-01 |
| 72 | hsa-miR-208b | 78 | 76 | 1.03 | 4.75E-01 | 0.52 | 4.95E-01 |
| 73 | hsa-miR-1972 | 279 | 325 | 0.86 | 4.90E-01 | 0.56 | 5.09E-01 |
| 74 | hsa-miR-1977 | 45 | 33 | 1.35 | 4.97E-01 | 0.40 | 4.91E-01 |
| 75 | hsa-miR-96* | 77 | 88 | 0.88 | 5.07E-01 | 0.55 | 5.26E-01 |
| 76 | hsa-miR-486-5p | 28549 | 31051 | 0.92 | 5.27E-01 | 0.54 | 5.40E-01 |
| 77 | hsa-miR-1979 | 278 | 252 | 1.10 | 5.54E-01 | 0.42 | 5.43E-01 |
| 78 | hsa-miR-29b-2* | 71 | 65 | 1.09 | 5.73E-01 | 0.43 | 5.80E-01 |
| 79 | hsa-miR-1322 | 142 | 136 | 1.04 | 5.83E-01 | 0.53 | 5.68E-01 |
| 80 | hsa-miR-144 | 3916 | 4339 | 0.90 | 6.20E-01 | 0.56 | 6.08E-01 |
| 81 | hsa-miR-619 | 52 | 64 | 0.82 | 6.20E-01 | 0.56 | 6.17E-01 |
| 82 | hsa-miR-1259 | 32 | 27 | 1.21 | 6.76E-01 | 0.47 | 6.80E-01 |
| 83 | hsa-miR-296-3p | 90 | 95 | 0.95 | 6.87E-01 | 0.48 | 6.70E-01 |
| 84 | hsa-miR-1250 | 85 | 59 | 1.43 | 6.88E-01 | 0.46 | 6.72E-01 |
| 85 | hsa-miR-524-3p | 36 | 37 | 0.99 | 6.88E-01 | 0.52 | 7.00E-01 |
| 86 | hsa-miR-145 | 86 | 105 | 0.81 | 7.35E-01 | 0.55 | 7.26E-01 |
| 87 | hsa-miR-1253 | 61 | 62 | 0.97 | 7.50E-01 | 0.54 | 7.53E-01 |
| 88 | hsa-miR-365 | 59 | 50 | 1.19 | 7.62E-01 | 0.46 | 7.69E-01 |
| 89 | hsa-miR-125b | 109 | 86 | 1.27 | 7.75E-01 | 0.44 | 7.68E-01 |
| 90 | hsa-miR-671-3p | 51 | 51 | 1.02 | 7.85E-01 | 0.51 | 7.86E-01 |
| 91 | hsa-miR-320a | 11598 | 10990 | 1.06 | 7.95E-01 | 0.52 | 7.90E-01 |
| 92 | hsa-miR-1181 | 238 | 230 | 1.04 | 8.20E-01 | 0.48 | 8.23E-01 |
| 93 | hsa-miR-1274a | 84 | 78 | 1.09 | 8.36E-01 | 0.46 | 8.46E-01 |
| 94 | hsa-miR-181a* | 68 | 67 | 1.02 | 8.76E-01 | 0.54 | 8.81E-01 |
| 95 | hsa-miR-1976 | 344 | 276 | 1.25 | 8.85E-01 | 0.46 | 8.77E-01 |
| 96 | hsa-miR-34c-5p | 52 | 53 | 0.99 | 8.85E-01 | 0.51 | 8.94E-01 |

Figure 1 (cont.)

| 97 | hsa-miR-542-5p | 74 | 77 | 0.97 | 8.91E-01 | 0.54 | 9.02E-01 |
| 98 | hsa-miR-630 | 42 | 39 | 1.06 | 9.25E-01 | 0.51 | 9.27E-01 |
| 99 | hsa-miR-1183 | 160 | 175 | 0.91 | 9.42E-01 | 0.51 | 9.40E-01 |

Figure 2  CD vs UC

| SEQ ID NO: | mirna | median g1 | median g2 | qmedian | ttest adjp | AUC | limma adjp |
|---|---|---|---|---|---|---|---|
| 100 | hsa-miR-1301 | 111 | 210 | 0.53 | 3.86E-07 | 0.89 | 6.63E-06 |
| 101 | hsa-miR-1826 | 144 | 248 | 0.58 | 4.73E-07 | 0.87 | 6.70E-06 |
| 102 | hsa-miR-377 | 96 | 190 | 0.51 | 3.35E-06 | 0.86 | 7.32E-06 |
| 103 | hsa-miR-1184 | 96 | 237 | 0.41 | 1.00E-05 | 0.85 | 6.63E-06 |
| 104 | hsa-miR-101* | 103 | 47 | 2.17 | 1.37E-05 | 0.16 | 6.70E-06 |
| 105 | hsa-miR-593* | 221 | 379 | 0.58 | 2.37E-05 | 0.82 | 6.01E-05 |
| 106 | hsa-miR-519c-5p | 94 | 172 | 0.55 | 3.41E-05 | 0.83 | 1.96E-05 |
| 107 | hsa-miR-330-3p | 205 | 396 | 0.52 | 3.41E-05 | 0.84 | 7.31E-05 |
| 108 | hsa-miR-410 | 85 | 151 | 0.56 | 3.69E-05 | 0.82 | 7.31E-05 |
| 109 | hsa-miR-15a* | 117 | 59 | 1.98 | 4.70E-05 | 0.18 | 7.31E-05 |
| 1 | hsa-miR-1973 | 149 | 281 | 0.53 | 5.74E-05 | 0.81 | 8.41E-05 |
| 110 | hsa-miR-1295 | 82 | 161 | 0.51 | 5.74E-05 | 0.82 | 8.12E-05 |
| 111 | hsa-miR-431 | 120 | 220 | 0.54 | 5.74E-05 | 0.82 | 7.31E-05 |
| 112 | hsa-miR-564 | 112 | 213 | 0.52 | 7.08E-05 | 0.80 | 7.56E-05 |
| 113 | hsa-miR-575 | 91 | 167 | 0.55 | 9.50E-05 | 0.81 | 9.60E-05 |
| 114 | hsa-miR-301b | 144 | 222 | 0.65 | 1.23E-04 | 0.80 | 4.08E-04 |
| 115 | hsa-miR-518a-5p | 104 | 200 | 0.52 | 1.71E-04 | 0.80 | 1.39E-04 |
| 116 | hsa-miR-1469 | 115 | 184 | 0.62 | 3.46E-04 | 0.81 | 2.63E-04 |
| 4 | hsa-miR-1251 | 89 | 141 | 0.63 | 3.82E-04 | 0.77 | 2.29E-04 |
| 117 | hsa-miR-455-3p | 82 | 176 | 0.47 | 5.11E-04 | 0.78 | 3.58E-04 |
| 118 | hsa-miR-32 | 175 | 265 | 0.66 | 5.92E-04 | 0.78 | 6.88E-04 |
| 119 | hsa-miR-526a | 85 | 148 | 0.58 | 6.47E-04 | 0.78 | 3.79E-04 |
| 120 | hsa-miR-519a* | 76 | 137 | 0.56 | 7.68E-04 | 0.76 | 3.92E-04 |
| 2 | hsa-miR-621 | 155 | 335 | 0.46 | 7.85E-04 | 0.80 | 3.92E-04 |
| 121 | hsa-miR-421 | 173 | 105 | 1.65 | 1.10E-03 | 0.23 | 6.82E-04 |
| 122 | hsa-miR-520a-5p | 61 | 139 | 0.44 | 1.14E-03 | 0.76 | 7.92E-04 |
| 6 | hsa-miR-127-5p | 61 | 141 | 0.43 | 1.27E-03 | 0.75 | 5.96E-04 |
| 123 | hsa-miR-922 | 76 | 127 | 0.60 | 1.27E-03 | 0.76 | 8.87E-04 |
| 124 | hsa-miR-188-3p | 95 | 158 | 0.60 | 1.27E-03 | 0.75 | 1.41E-03 |
| 125 | hsa-miR-588 | 62 | 106 | 0.59 | 1.27E-03 | 0.76 | 1.15E-03 |
| 126 | hsa-miR-146b-3p | 53 | 102 | 0.52 | 1.38E-03 | 0.76 | 1.44E-03 |
| 127 | hsa-miR-541 | 62 | 117 | 0.53 | 1.44E-03 | 0.75 | 1.39E-03 |
| 128 | hsa-let-7i* | 119 | 216 | 0.55 | 1.44E-03 | 0.76 | 1.47E-03 |
| 129 | hsa-miR-517* | 84 | 142 | 0.59 | 1.44E-03 | 0.75 | 1.31E-03 |
| 130 | hsa-miR-361-5p | 449 | 231 | 1.94 | 1.68E-03 | 0.23 | 1.09E-03 |
| 131 | hsa-miR-210 | 754 | 382 | 1.97 | 1.74E-03 | 0.25 | 8.54E-04 |
| 132 | hsa-miR-522* | 97 | 170 | 0.57 | 1.84E-03 | 0.77 | 1.46E-03 |
| 3 | hsa-miR-363 | 5045 | 10707 | 0.47 | 1.89E-03 | 0.76 | 1.21E-03 |
| 133 | hsa-miR-640 | 72 | 121 | 0.60 | 2.05E-03 | 0.73 | 1.59E-03 |

Figure 2 (cont.)

| | | | | | | | |
|---|---|---|---|---|---|---|---|
| 134 | hsa-miR-376c | 122 | 211 | 0.58 | 2.05E-03 | 0.73 | 1.46E-03 |
| 135 | hsa-miR-1200 | 73 | 114 | 0.64 | 2.30E-03 | 0.74 | 2.06E-03 |
| 136 | hsa-miR-744 | 280 | 156 | 1.79 | 2.37E-03 | 0.24 | 1.75E-03 |
| 137 | hsa-miR-548p | 68 | 126 | 0.54 | 2.41E-03 | 0.73 | 2.22E-03 |
| 138 | hsa-miR-509-3-5p | 122 | 197 | 0.62 | 3.29E-03 | 0.75 | 3.57E-03 |
| 10 | hsa-miR-527 | 73 | 149 | 0.49 | 3.32E-03 | 0.74 | 2.07E-03 |
| 139 | hsa-miR-590-5p | 299 | 497 | 0.60 | 4.06E-03 | 0.74 | 3.57E-03 |
| 140 | hsa-miR-518e* | 84 | 140 | 0.60 | 4.55E-03 | 0.73 | 4.24E-03 |
| 141 | hsa-miR-490-5p | 103 | 166 | 0.62 | 5.40E-03 | 0.74 | 6.97E-03 |
| 13 | hsa-miR-1275 | 170 | 94 | 1.81 | 5.92E-03 | 0.25 | 4.44E-03 |
| 142 | hsa-miR-452* | 144 | 261 | 0.55 | 6.86E-03 | 0.74 | 4.71E-03 |
| 143 | hsa-miR-1324 | 68 | 121 | 0.56 | 7.64E-03 | 0.73 | 9.18E-03 |
| 15 | hsa-miR-556-5p | 65 | 110 | 0.59 | 7.74E-03 | 0.71 | 8.76E-03 |
| 144 | hsa-miR-1226* | 142 | 216 | 0.66 | 7.86E-03 | 0.71 | 1.41E-02 |
| 145 | hsa-miR-1266 | 78 | 134 | 0.58 | 8.15E-03 | 0.70 | 7.69E-03 |
| 146 | hsa-miR-143* | 75 | 126 | 0.59 | 8.44E-03 | 0.71 | 8.64E-03 |
| 147 | hsa-miR-646 | 168 | 288 | 0.58 | 8.53E-03 | 0.72 | 8.29E-03 |
| 148 | hsa-miR-192* | 76 | 126 | 0.60 | 9.86E-03 | 0.72 | 1.18E-02 |
| 149 | hsa-miR-128 | 275 | 420 | 0.66 | 9.88E-03 | 0.69 | 1.42E-02 |
| 19 | hsa-miR-31* | 93 | 175 | 0.53 | 1.02E-02 | 0.73 | 8.24E-03 |
| 150 | hsa-miR-515-5p | 102 | 173 | 0.59 | 1.03E-02 | 0.73 | 1.25E-02 |
| 151 | hsa-miR-1231 | 69 | 113 | 0.61 | 1.12E-02 | 0.72 | 1.13E-02 |
| 152 | hsa-miR-199a-3p | 744 | 1320 | 0.56 | 1.38E-02 | 0.70 | 1.38E-02 |
| 153 | hsa-miR-628-5p | 78 | 125 | 0.63 | 1.40E-02 | 0.70 | 1.31E-02 |
| 154 | hsa-miR-1205 | 71 | 113 | 0.63 | 1.42E-02 | 0.69 | 1.42E-02 |
| 155 | hsa-miR-767-5p | 102 | 175 | 0.59 | 1.62E-02 | 0.71 | 1.37E-02 |
| 156 | hsa-miR-489 | 114 | 177 | 0.65 | 1.75E-02 | 0.70 | 1.81E-02 |
| 157 | hsa-miR-509-5p | 135 | 273 | 0.49 | 1.99E-02 | 0.68 | 1.77E-02 |
| 158 | hsa-miR-505* | 83 | 127 | 0.65 | 2.09E-02 | 0.67 | 2.62E-02 |
| 159 | hsa-miR-217 | 80 | 138 | 0.58 | 2.24E-02 | 0.69 | 1.79E-02 |
| 160 | hsa-miR-933 | 124 | 213 | 0.58 | 2.89E-02 | 0.67 | 2.34E-02 |
| 161 | hsa-miR-451 | 973 | 1651 | 0.59 | 3.14E-02 | 0.69 | 2.17E-02 |
| 162 | hsa-miR-15a | 5534 | 9695 | 0.57 | 3.24E-02 | 0.69 | 2.95E-02 |
| 163 | hsa-miR-629 | 159 | 58 | 2.76 | 3.71E-02 | 0.35 | 2.21E-02 |

Figure 3    HC vs IBD (=CD + UC)

| SEQ ID NO: | mirna | median g1 | median g2 | qmedian | ttest adjp | AUC | limma adjp |
|---|---|---|---|---|---|---|---|
| 163 | hsa-miR-885-5p | 37 | 172 | 0.21 | 4.87E-16 | 0.93 | 3.55E-16 |
| 164 | hsa-miR-374a | 245 | 750 | 0.33 | 2.36E-14 | 0.91 | 3.41E-13 |
| 165 | hsa-miR-523* | 160 | 73 | 2.20 | 3.06E-13 | 0.10 | 3.98E-11 |
| 44 | hsa-miR-29b | 295 | 916 | 0.32 | 6.77E-12 | 0.90 | 1.25E-12 |
| 80 | hsa-miR-144 | 1311 | 4100 | 0.32 | 5.40E-11 | 0.90 | 2.89E-13 |
| 87 | hsa-miR-1253 | 104 | 57 | 1.83 | 5.40E-11 | 0.14 | 2.91E-09 |
| 128 | hsa-let-7i* | 308 | 152 | 2.03 | 5.40E-11 | 0.14 | 3.55E-09 |
| 166 | hsa-let-7f | 310 | 1450 | 0.21 | 7.56E-11 | 0.89 | 1.25E-12 |

Figure 3 (cont.)

| 167 | hsa-miR-142-5p | 631 | 2484 | 0.25 | 7.56E-11 | 0.88 | 9.38E-12 |
|---|---|---|---|---|---|---|---|
| 168 | hsa-miR-362-3p | 105 | 266 | 0.39 | 7.56E-11 | 0.90 | 5.37E-12 |
| 169 | hsa-miR-1228* | 346 | 906 | 0.38 | 1.09E-10 | 0.89 | 2.10E-11 |
| 170 | hsa-miR-26b | 352 | 1288 | 0.27 | 1.09E-10 | 0.86 | 8.64E-11 |
| 138 | hsa-miR-509-3-5p | 276 | 143 | 1.94 | 1.86E-10 | 0.16 | 2.16E-08 |
| 171 | hsa-miR-16 | 9684 | 24219 | 0.40 | 2.14E-10 | 0.87 | 1.37E-10 |
| 172 | hsa-miR-30e | 330 | 1222 | 0.27 | 2.33E-10 | 0.88 | 2.32E-12 |
| 173 | hsa-miR-34b | 118 | 424 | 0.28 | 2.33E-10 | 0.87 | 2.12E-12 |
| 62 | hsa-miR-22* | 44 | 131 | 0.34 | 3.43E-10 | 0.87 | 3.59E-12 |
| 139 | hsa-miR-590-5p | 180 | 404 | 0.44 | 4.45E-10 | 0.85 | 1.42E-08 |
| 174 | hsa-miR-205 | 65 | 430 | 0.15 | 6.35E-10 | 0.87 | 7.62E-12 |
| 175 | hsa-miR-9* | 105 | 54 | 1.94 | 7.32E-10 | 0.15 | 1.42E-08 |
| 176 | hsa-let-7c | 392 | 1752 | 0.22 | 7.32E-10 | 0.87 | 5.46E-12 |
| 177 | hsa-miR-611 | 142 | 81 | 1.76 | 1.31E-09 | 0.17 | 1.08E-07 |
| 178 | hsa-miR-1825 | 77 | 226 | 0.34 | 1.41E-09 | 0.85 | 1.37E-10 |
| 179 | hsa-miR-221* | 148 | 73 | 2.03 | 1.67E-09 | 0.15 | 4.40E-08 |
| 180 | hsa-miR-25 | 2728 | 9033 | 0.30 | 2.00E-09 | 0.88 | 1.92E-12 |
| 181 | hsa-miR-21 | 1309 | 3600 | 0.36 | 2.06E-09 | 0.89 | 2.10E-12 |
| 182 | hsa-let-7e | 105 | 442 | 0.24 | 2.10E-09 | 0.88 | 1.81E-12 |
| 183 | hsa-miR-20a | 7134 | 15691 | 0.45 | 2.53E-09 | 0.87 | 7.61E-11 |
| 184 | hsa-miR-1229 | 513 | 2088 | 0.25 | 2.62E-09 | 0.85 | 3.43E-11 |
| 185 | hsa-miR-101 | 752 | 1904 | 0.39 | 2.69E-09 | 0.85 | 6.48E-11 |
| 186 | hsa-miR-144* | 381 | 918 | 0.42 | 3.11E-09 | 0.87 | 2.64E-11 |
| 187 | hsa-miR-545 | 128 | 79 | 1.63 | 4.98E-09 | 0.18 | 1.08E-07 |
| 188 | hsa-miR-663b | 116 | 67 | 1.73 | 6.73E-09 | 0.19 | 1.07E-06 |
| 189 | hsa-miR-126 | 2551 | 7213 | 0.35 | 1.12E-08 | 0.85 | 7.35E-10 |
| 190 | hsa-miR-223 | 584 | 3257 | 0.18 | 1.29E-08 | 0.85 | 2.92E-11 |
| 191 | hsa-miR-30a | 248 | 713 | 0.35 | 1.29E-08 | 0.85 | 2.89E-10 |
| 161 | hsa-miR-15a | 3176 | 8199 | 0.39 | 1.47E-08 | 0.84 | 1.12E-09 |
| 192 | hsa-miR-374b | 308 | 797 | 0.39 | 1.51E-08 | 0.82 | 2.20E-08 |
| 193 | hsa-miR-1539 | 121 | 77 | 1.56 | 2.08E-08 | 0.20 | 2.72E-07 |
| 194 | hsa-miR-192 | 2275 | 4825 | 0.47 | 3.79E-08 | 0.84 | 2.65E-09 |
| 195 | hsa-miR-17 | 12055 | 21341 | 0.56 | 4.03E-08 | 0.83 | 2.32E-08 |
| 196 | hsa-miR-1268 | 225 | 772 | 0.29 | 4.06E-08 | 0.85 | 3.41E-11 |
| 197 | hsa-miR-574-3p | 936 | 2944 | 0.32 | 4.42E-08 | 0.82 | 5.83E-08 |
| 198 | hsa-miR-19a | 1838 | 5695 | 0.32 | 4.42E-08 | 0.83 | 2.63E-10 |
| 199 | hsa-let-7g | 247 | 1384 | 0.18 | 4.77E-08 | 0.83 | 2.49E-09 |
| 200 | hsa-miR-424 | 348 | 794 | 0.44 | 5.75E-08 | 0.86 | 4.04E-10 |
| 201 | hsa-miR-30c | 770 | 2930 | 0.26 | 5.96E-08 | 0.84 | 6.65E-11 |
| 202 | hsa-miR-664 | 109 | 362 | 0.30 | 5.96E-08 | 0.87 | 2.12E-12 |
| 203 | hsa-miR-99b | 213 | 131 | 1.62 | 5.96E-08 | 0.21 | 1.26E-06 |
| 204 | hsa-miR-29c | 337 | 1189 | 0.28 | 7.08E-08 | 0.82 | 1.59E-09 |
| 205 | hsa-miR-454 | 181 | 455 | 0.40 | 8.13E-08 | 0.83 | 4.15E-09 |
| 206 | hsa-miR-23b | 1534 | 3675 | 0.42 | 8.13E-08 | 0.83 | 2.96E-10 |
| 207 | hsa-miR-1271 | 175 | 94 | 1.87 | 8.56E-08 | 0.20 | 8.51E-07 |
| 208 | hsa-miR-574-5p | 487 | 3315 | 0.15 | 9.39E-08 | 0.85 | 4.09E-12 |
| 209 | hsa-let-7i | 521 | 1952 | 0.27 | 9.39E-08 | 0.84 | 8.72E-11 |
| 210 | hsa-miR-1286 | 158 | 93 | 1.69 | 1.00E-07 | 0.22 | 6.26E-06 |
| 211 | hsa-miR-19b | 7067 | 16011 | 0.44 | 1.16E-07 | 0.82 | 2.20E-08 |
| 212 | hsa-miR-197 | 453 | 1310 | 0.35 | 1.21E-07 | 0.83 | 1.48E-08 |
| 213 | hsa-miR-570 | 118 | 50 | 2.34 | 1.55E-07 | 0.13 | 3.56E-09 |

Figure 3 (cont.)

| | | | | | | | |
|---|---|---|---|---|---|---|---|
| 214 | hsa-miR-518f* | 185 | 114 | 1.62 | 1.65E-07 | 0.20 | 1.07E-05 |
| 215 | hsa-miR-328 | 44 | 122 | 0.36 | 1.77E-07 | 0.81 | 5.12E-08 |
| 216 | hsa-miR-26a | 6404 | 12644 | 0.51 | 1.82E-07 | 0.81 | 1.87E-07 |
| 217 | hsa-miR-551b | 103 | 53 | 1.93 | 1.91E-07 | 0.20 | 3.46E-07 |
| 218 | hsa-miR-215 | 207 | 356 | 0.58 | 2.18E-07 | 0.80 | 1.15E-06 |
| 219 | hsa-let-7b | 1145 | 3586 | 0.32 | 2.30E-07 | 0.81 | 2.64E-08 |
| 220 | hsa-miR-1234 | 1549 | 5505 | 0.28 | 3.09E-07 | 0.80 | 6.43E-08 |
| 221 | hsa-miR-20b | 8146 | 14381 | 0.57 | 3.89E-07 | 0.81 | 1.44E-07 |
| 222 | hsa-miR-1260 | 368 | 1048 | 0.35 | 4.90E-07 | 0.83 | 2.20E-08 |
| 223 | hsa-miR-1280 | 606 | 1162 | 0.52 | 4.90E-07 | 0.80 | 2.13E-07 |
| 224 | hsa-miR-106a | 9490 | 18626 | 0.51 | 4.97E-07 | 0.80 | 1.93E-07 |
| 225 | hsa-miR-27b | 554 | 1259 | 0.44 | 5.23E-07 | 0.80 | 1.32E-07 |
| 226 | hsa-let-7g* | 139 | 90 | 1.55 | 6.28E-07 | 0.20 | 8.42E-06 |
| 227 | hsa-miR-298 | 185 | 98 | 1.89 | 6.38E-07 | 0.19 | 2.76E-06 |
| 228 | hsa-miR-595 | 102 | 370 | 0.28 | 6.38E-07 | 0.81 | 9.78E-09 |
| 100 | hsa-miR-1301 | 246 | 154 | 1.59 | 7.68E-07 | 0.22 | 7.32E-06 |
| 229 | hsa-miR-1207-5p | 264 | 507 | 0.52 | 7.85E-07 | 0.77 | 1.72E-06 |
| 14 | hsa-miR-1324 | 153 | 95 | 1.61 | 8.83E-07 | 0.22 | 7.99E-06 |
| 230 | hsa-miR-28-3p | 158 | 248 | 0.64 | 1.02E-06 | 0.82 | 8.42E-06 |
| 103 | hsa-miR-1184 | 276 | 159 | 1.73 | 1.16E-06 | 0.23 | 1.95E-05 |
| 42 | hsa-miR-499-3p | 111 | 52 | 2.13 | 1.23E-06 | 0.17 | 2.16E-07 |
| 231 | hsa-miR-146a | 302 | 918 | 0.33 | 1.23E-06 | 0.80 | 7.73E-08 |
| 232 | hsa-miR-1273 | 159 | 77 | 2.07 | 1.32E-06 | 0.23 | 7.41E-06 |
| 233 | hsa-miR-27a | 1147 | 2357 | 0.49 | 1.48E-06 | 0.81 | 7.73E-08 |
| 234 | hsa-miR-660 | 506 | 1225 | 0.41 | 1.48E-06 | 0.79 | 3.29E-07 |
| 235 | hsa-miR-584 | 74 | 183 | 0.41 | 1.63E-06 | 0.81 | 2.59E-08 |
| 236 | hsa-miR-422a | 226 | 447 | 0.51 | 1.84E-06 | 0.77 | 8.04E-06 |
| 52 | hsa-miR-199b-3p | 472 | 1052 | 0.45 | 1.99E-06 | 0.80 | 7.73E-08 |
| 237 | hsa-miR-635 | 130 | 80 | 1.62 | 2.53E-06 | 0.23 | 1.82E-05 |
| 238 | hsa-miR-130a | 2345 | 5109 | 0.46 | 2.84E-06 | 0.79 | 1.96E-06 |
| 239 | hsa-miR-449b* | 225 | 567 | 0.40 | 2.87E-06 | 0.80 | 4.40E-08 |
| 240 | hsa-miR-93 | 8892 | 17134 | 0.52 | 2.87E-06 | 0.80 | 5.59E-07 |
| 241 | hsa-miR-301a | 475 | 956 | 0.50 | 3.12E-06 | 0.79 | 4.80E-06 |
| 242 | hsa-miR-194 | 4017 | 9417 | 0.43 | 3.12E-06 | 0.79 | 2.88E-07 |
| 243 | hsa-miR-107 | 3338 | 5786 | 0.58 | 3.70E-06 | 0.78 | 3.17E-06 |
| 95 | hsa-miR-1976 | 89 | 314 | 0.28 | 4.01E-06 | 0.79 | 6.51E-07 |
| 13 | hsa-miR-1275 | 63 | 118 | 0.54 | 4.08E-06 | 0.79 | 8.68E-07 |
| 244 | hsa-miR-29a | 798 | 2230 | 0.36 | 4.08E-06 | 0.78 | 3.46E-07 |
| 245 | hsa-miR-483-3p | 112 | 384 | 0.29 | 4.41E-06 | 0.78 | 2.02E-07 |
| 246 | hsa-miR-877* | 167 | 420 | 0.40 | 4.66E-06 | 0.78 | 1.07E-06 |
| 247 | hsa-miR-30d | 3681 | 8483 | 0.43 | 4.73E-06 | 0.79 | 1.15E-06 |
| 119 | hsa-miR-526a | 178 | 102 | 1.75 | 5.14E-06 | 0.26 | 5.97E-05 |
| 248 | hsa-miR-7 | 36 | 129 | 0.28 | 5.14E-06 | 0.78 | 2.72E-07 |
| 249 | hsa-miR-149* | 185 | 301 | 0.61 | 5.14E-06 | 0.74 | 4.31E-05 |
| 250 | hsa-miR-1913 | 232 | 459 | 0.51 | 5.14E-06 | 0.78 | 3.14E-06 |
| 251 | hsa-miR-148a | 723 | 1151 | 0.63 | 5.25E-06 | 0.77 | 2.23E-05 |
| 125 | hsa-miR-588 | 149 | 81 | 1.84 | 5.78E-06 | 0.21 | 1.29E-05 |
| 252 | hsa-miR-92a | 3888 | 8536 | 0.46 | 7.04E-06 | 0.79 | 5.42E-07 |
| 253 | hsa-miR-338-3p | 176 | 300 | 0.59 | 8.79E-06 | 0.73 | 1.64E-04 |
| 254 | hsa-miR-187* | 190 | 95 | 2.00 | 1.08E-05 | 0.23 | 3.40E-05 |
| 255 | hsa-miR-487a | 106 | 62 | 1.70 | 1.12E-05 | 0.22 | 2.33E-05 |

Figure 3 (cont.)

| | | | | | | | |
|---|---|---|---|---|---|---|---|
| 256 | hsa-miR-22 | 7737 | 13080 | 0.59 | 1.53E-05 | 0.76 | 1.38E-05 |
| 118 | hsa-miR-32 | 136 | 225 | 0.61 | 1.59E-05 | 0.79 | 1.80E-04 |
| 257 | hsa-miR-766 | 724 | 1908 | 0.38 | 1.59E-05 | 0.76 | 8.04E-06 |
| 258 | hsa-miR-196a* | 154 | 88 | 1.76 | 1.77E-05 | 0.23 | 3.09E-05 |
| 259 | hsa-let-7a | 875 | 1688 | 0.52 | 2.15E-05 | 0.77 | 1.66E-05 |
| 260 | hsa-miR-18a | 3469 | 5492 | 0.63 | 2.18E-05 | 0.78 | 5.26E-06 |
| 261 | hsa-miR-222 | 597 | 1446 | 0.41 | 2.57E-05 | 0.76 | 3.11E-06 |
| 262 | hsa-miR-96 | 243 | 401 | 0.61 | 2.59E-05 | 0.75 | 8.43E-05 |
| 263 | hsa-miR-1255b | 113 | 74 | 1.53 | 2.86E-05 | 0.22 | 1.02E-04 |
| 76 | hsa-miR-486-5p | 19129 | 31806 | 0.60 | 2.98E-05 | 0.76 | 1.71E-04 |
| 264 | hsa-miR-143 | 463 | 872 | 0.53 | 3.47E-05 | 0.76 | 1.46E-05 |
| 265 | hsa-miR-221 | 253 | 522 | 0.48 | 3.54E-05 | 0.75 | 1.28E-05 |
| 266 | hsa-miR-1228 | 686 | 2208 | 0.31 | 4.58E-05 | 0.74 | 2.96E-05 |
| 267 | hsa-miR-153 | 151 | 98 | 1.54 | 5.47E-05 | 0.26 | 2.68E-04 |
| 268 | hsa-miR-1281 | 151 | 376 | 0.40 | 5.69E-05 | 0.74 | 5.65E-05 |
| 269 | hsa-miR-497 | 243 | 156 | 1.56 | 6.94E-05 | 0.24 | 2.50E-05 |
| 104 | hsa-miR-101* | 112 | 71 | 1.59 | 7.24E-05 | 0.29 | 2.32E-04 |
| 99 | hsa-miR-1183 | 106 | 164 | 0.65 | 8.78E-05 | 0.73 | 3.98E-04 |
| 270 | hsa-miR-1908 | 183 | 294 | 0.62 | 9.05E-05 | 0.72 | 6.29E-04 |
| 75 | hsa-miR-96* | 127 | 76 | 1.67 | 9.55E-05 | 0.25 | 3.03E-04 |
| 271 | hsa-miR-518b | 70 | 109 | 0.65 | 1.12E-04 | 0.74 | 8.50E-05 |
| 272 | hsa-miR-362-5p | 135 | 239 | 0.57 | 1.30E-04 | 0.76 | 2.48E-05 |
| 10 | hsa-miR-527 | 187 | 102 | 1.83 | 1.44E-04 | 0.27 | 2.05E-04 |
| 273 | hsa-miR-23a | 2296 | 4524 | 0.51 | 1.49E-04 | 0.74 | 7.33E-06 |
| 151 | hsa-miR-199a-3p | 538 | 1108 | 0.49 | 1.74E-04 | 0.74 | 2.47E-05 |
| 274 | hsa-miR-376a | 170 | 113 | 1.51 | 1.92E-04 | 0.28 | 3.93E-04 |
| 3 | hsa-miR-363 | 4215 | 7978 | 0.53 | 2.23E-04 | 0.73 | 2.24E-04 |
| 106 | hsa-miR-519c-5p | 191 | 119 | 1.60 | 2.23E-04 | 0.28 | 6.53E-04 |
| 275 | hsa-miR-650 | 174 | 115 | 1.51 | 2.35E-04 | 0.26 | 3.84E-04 |
| 276 | hsa-miR-340 | 217 | 350 | 0.62 | 2.85E-04 | 0.72 | 1.29E-03 |
| 15 | hsa-miR-556-5p | 131 | 67 | 1.94 | 3.31E-04 | 0.27 | 2.62E-04 |
| 277 | hsa-miR-30b | 3431 | 6031 | 0.57 | 4.83E-04 | 0.73 | 2.50E-05 |
| 2 | hsa-miR-621 | 334 | 210 | 1.59 | 4.86E-04 | 0.31 | 1.52E-03 |
| 278 | hsa-miR-490-3p | 121 | 75 | 1.61 | 5.23E-04 | 0.27 | 5.26E-04 |
| 279 | hsa-miR-342-5p | 63 | 108 | 0.59 | 6.27E-04 | 0.71 | 1.09E-04 |
| 51 | hsa-miR-139-3p | 131 | 78 | 1.69 | 7.31E-04 | 0.24 | 2.85E-04 |
| 280 | hsa-miR-634 | 387 | 934 | 0.41 | 7.45E-04 | 0.71 | 5.65E-04 |
| 281 | hsa-miR-151-3p | 566 | 981 | 0.58 | 1.03E-03 | 0.70 | 5.87E-04 |
| 282 | hsa-miR-125a-5p | 70 | 107 | 0.66 | 1.27E-03 | 0.70 | 1.48E-03 |
| 283 | hsa-miR-378 | 370 | 597 | 0.62 | 2.18E-03 | 0.70 | 1.45E-03 |
| 284 | hsa-miR-335 | 377 | 636 | 0.59 | 2.19E-03 | 0.69 | 2.15E-03 |
| 115 | hsa-miR-518a-5p | 188 | 125 | 1.51 | 2.65E-03 | 0.32 | 4.23E-03 |
| 285 | hsa-miR-216b | 145 | 88 | 1.65 | 2.98E-03 | 0.29 | 2.99E-03 |
| 286 | hsa-miR-423-3p | 149 | 241 | 0.62 | 3.34E-03 | 0.73 | 1.80E-03 |
| 287 | hsa-miR-1224-3p | 414 | 1009 | 0.41 | 4.56E-03 | 0.70 | 1.32E-03 |
| 123 | hsa-miR-922 | 209 | 94 | 2.22 | 5.56E-03 | 0.31 | 1.98E-03 |
| 122 | hsa-miR-520a-5p | 130 | 83 | 1.56 | 5.57E-03 | 0.34 | 1.07E-02 |
| 288 | hsa-miR-1249 | 363 | 844 | 0.43 | 7.28E-03 | 0.69 | 8.18E-03 |
| 289 | hsa-miR-1305 | 112 | 63 | 1.78 | 7.34E-03 | 0.33 | 5.37E-03 |
| 290 | hsa-miR-18b | 460 | 836 | 0.55 | 7.70E-03 | 0.67 | 4.98E-03 |
| 291 | hsa-miR-532-5p | 467 | 814 | 0.57 | 7.86E-03 | 0.69 | 9.91E-03 |

Figure 3 (cont.)

| 160 | hsa-miR-451 | 732 | 1283 | 0.57 | 9.20E-03 | 0.67 | 1.84E-02 |
|---|---|---|---|---|---|---|---|
| 153 | hsa-miR-1205 | 123 | 80 | 1.52 | 1.03E-02 | 0.34 | 1.09E-02 |
| 292 | hsa-miR-500 | 162 | 288 | 0.56 | 1.04E-02 | 0.67 | 1.04E-02 |
| 293 | hsa-miR-608 | 59 | 103 | 0.57 | 1.06E-02 | 0.66 | 4.13E-03 |
| 294 | hsa-miR-150 | 712 | 1614 | 0.44 | 1.06E-02 | 0.67 | 6.97E-03 |
| 295 | hsa-miR-320d | 499 | 793 | 0.63 | 1.13E-02 | 0.66 | 8.58E-03 |
| 296 | hsa-let-7d | 2212 | 4293 | 0.52 | 1.42E-02 | 0.67 | 1.10E-02 |
| 297 | hsa-miR-433 | 120 | 69 | 1.75 | 1.96E-02 | 0.31 | 7.85E-03 |
| 6 | hsa-miR-127-5p | 141 | 86 | 1.65 | 2.09E-02 | 0.39 | 4.04E-02 |
| 298 | hsa-miR-550* | 93 | 144 | 0.65 | 2.69E-02 | 0.65 | 1.92E-02 |
| 299 | hsa-miR-199a-5p | 194 | 326 | 0.60 | 3.27E-02 | 0.65 | 1.36E-02 |

Figure 4    miRNA-Signatures

| Signature | SEQ-ID NOs | miRNA -identifiers | Acc | Spec | Sens |
|---|---|---|---|---|---|
| SHI-1 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 | hsa-miR-1973, hsa-miR-621, hsa-miR-363, hsa-miR-1251, hsa-let-7d*, hsa-miR-127-5p, hsa-miR-136, hsa-miR-616, hsa-miR-548d-5p, hsa-miR-527, hsa-miR-622, hsa-miR-522, hsa-miR-1275, hsa-miR-1324, hsa-miR-556-5p, hsa-miR-29a*, hsa-miR-516b*, hsa-miR-576-3p, hsa-miR-31*, hsa-miR-620, hsa-miR-20a*, hsa-miR-599, hsa-miR-610, hsa-miR-302b, hsa-miR-892a, hsa-miR-1257, hsa-miR-208a, hsa-miR-591, hsa-miR-500*, hsa-miR-132, hsa-miR-10a, hsa-miR-509-3p, hsa-miR-1321, hsa-miR-203, hsa-miR-889, hsa-miR-1252, hsa-miR-1974, hsa-miR-186*, hsa-miR-1206, hsa-miR-145*, hsa-miR-1258, hsa-miR-499-3p, hsa-miR-892b, hsa-miR-29b, hsa-miR-1978, hsa-miR-134, hsa-miR-593, hsa-miR-373*, hsa-miR-887, hsa-miR-138, hsa-miR-139-3p, hsa-miR-199b-3p , hsa-miR-1254, hsa-miR-708, hsa-miR-29c*, hsa-miR-1180, hsa-miR-302a*, hsa-miR-626, hsa-miR-432*, hsa-miR-1914*, hsa-miR-148b*, hsa-miR-22*, hsa-miR-1274b, hsa-miR-1323, hsa-miR-598, hsa-miR-532-3p, hsa-miR-888, hsa-miR-342-3p, hsa-miR-103-2*, hsa-miR-631, hsa-miR-1975, hsa-miR-208b, hsa-miR-1972, hsa-miR-1977, hsa-miR-96*, hsa-miR-486-5p, hsa-miR-1979, hsa-miR-29b-2*, hsa-miR-1322, hsa-miR-144, hsa-miR-619, hsa-miR-1259, hsa-miR-296-3p, hsa-miR-1250, hsa-miR-524-3p, hsa-miR-145, hsa-miR-1253, hsa-miR-365, hsa-miR-125b, hsa-miR-671-3p, hsa-miR-320a, hsa-miR-1181, hsa-miR-1274a, hsa-miR-181a*, hsa-miR-1976, hsa-miR-34c-5p, hsa-miR-542-5p, hsa-miR-630, hsa-miR-1183 | 93.0% | | |

Figure 4 (cont.)

| | | | |
|---|---|---|---|
| SCU-1 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 | hsa-miR-1973, hsa-miR-621, hsa-miR-363, hsa-miR-1251, hsa-let-7d*, hsa-miR-127-5p, hsa-miR-136, hsa-miR-616, hsa-miR-548d-5p, hsa-miR-527, hsa-miR-622, hsa-miR-522, hsa-miR-1275, hsa-miR-1324, hsa-miR-556-5p, hsa-miR-29a*, hsa-miR-516b*, hsa-miR-576-3p, hsa-miR-31*, hsa-miR-620, hsa-miR-20a*, hsa-miR-599, hsa-miR-610, hsa-miR-302b, hsa-miR-892a, hsa-miR-1257, hsa-miR-208a, hsa-miR-591, hsa-miR-500*, hsa-miR-132, hsa-miR-10a, hsa-miR-509-3p, hsa-miR-1321, hsa-miR-203, hsa-miR-889, hsa-miR-1252, hsa-miR-1974, hsa-miR-186*, hsa-miR-1206, hsa-miR-145*, hsa-miR-1258, hsa-miR-499-3p, hsa-miR-892b, hsa-miR-29b, hsa-miR-1978, hsa-miR-134, hsa-miR-593, hsa-miR-373*, hsa-miR-887, hsa-miR-138, hsa-miR-139-3p, hsa-miR-199b-3p , hsa-miR-1254, hsa-miR-708, hsa-miR-29c*, hsa-miR-1180, hsa-miR-302a*, hsa-miR-626, hsa-miR-432*, hsa-miR-1914*, hsa-miR-148b*, hsa-miR-22*, hsa-miR-1274b, hsa-miR-1323, hsa-miR-598, hsa-miR-532-3p, hsa-miR-888, hsa-miR-342-3p, hsa-miR-103-2*, hsa-miR-631, hsa-miR-1975, hsa-miR-208b, hsa-miR-1972, hsa-miR-1977, hsa-miR-96*, hsa-miR-486-5p, hsa-miR-1979, hsa-miR-29b-2*, hsa-miR-1322, hsa-miR-144, hsa-miR-619, hsa-miR-1259, hsa-miR-296-3p, hsa-miR-1250, hsa-miR-524-3p, hsa-miR-145, hsa-miR-1253, hsa-miR-365, hsa-miR-125b, hsa-miR-671-3p, hsa-miR-320a, hsa-miR-1181, hsa-miR-1274a, hsa-miR-181a*, hsa-miR-1976, hsa-miR-34c-5p, hsa-miR-542-5p, hsa-miR-630, hsa-miR-1183 | 84.2% | |

Figure 5

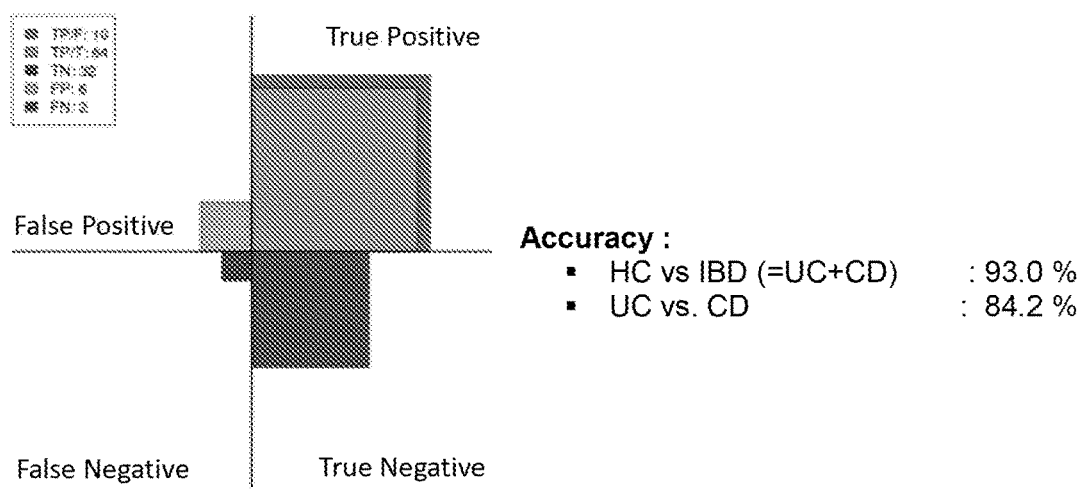

Accuracy :
- HC vs IBD (=UC+CD)   : 93.0 %
- UC vs. CD   : 84.2 %

| Seq ID NO: | mirna | fc | t | p | padj |
|---|---|---|---|---|---|
| 173 | hsa-miR-34b | 1.0 | -9.95E-01 | 3.24E-01 | 1.00E+00 |
| 102 | hsa-miR-377 | 0.6 | -5.52E+00 | 5.86E-07 | 5.02E-04 |
| 302 | hsa-miR-484 | 0.9 | -2.00E+00 | 5.00E-02 | 1.00E+00 |
| 208 | hsa-miR-574-5p | 1.0 | 3.90E-01 | 6.99E-01 | 1.00E+00 |
| 300 | hsa-miR-656 | 1.6 | 6.00E+00 | 9.39E-08 | 8.09E-05 |
| 136 | hsa-miR-744 | 51.7 | 5.11E+00 | 3.95E-06 | 3.37E-03 |
| 301 | hsa-miR-1247 | 0.6 | -4.59E+00 | 2.22E-05 | 1.86E-02 |
| 270 | hsa-miR-1908 | 1.4 | 2.27E+00 | 2.67E-02 | 1.00E+00 |

Fig. 6B: HC vs. IBD (HC vs CD+UC)

| Seq ID NO: | mirna | fc | t | p | padj |
|---|---|---|---|---|---|
| 303 | hsa-miR-98 | 0.6 | -8.42E+00 | 2.16E-14 | 1.59E-11 |
| 52 | hsa-miR-199b-3p | 0.5 | -1.67E+01 | 2.91E-35 | 2.51E-32 |
| 174 | hsa-miR-205 | 0.5 | -1.46E+01 | 8.14E-30 | 6.99E-27 |
| 253 | hsa-miR-338-3p | 0.5 | -9.20E+00 | 2.06E-16 | 1.58E-13 |
| 15 | hsa-miR-556-5p | 1.5 | 3.86E+00 | 1.64E-04 | 7.97E-02 |
| 304 | hsa-miR-1225-5p | 2.3 | 7.03E+00 | 5.97E-11 | 4.15E-08 |
| 64 | hsa-miR-1323 | 0.6 | -1.22E+01 | 1.57E-24 | 1.33E-21 |

Fig. 6C: HC vs. CD

| Seq ID NO: | mirna | fc | t | p | padj |
|---|---|---|---|---|---|
| 173 | hsa-miR-34b | 2.0 | 1.04E+01 | 1.77E-15 | 1.42E-12 |
| 167 | hsa-miR-142-5p | 2.7 | 1.10E+01 | 4.65E-20 | 3.93E-17 |
| 174 | hsa-miR-205 | 2.0 | 1.11E+01 | 1.11E-16 | 9.07E-14 |
| 200 | hsa-miR-424 | 2.3 | 1.08E+01 | 4.84E-19 | 4.06E-16 |
| 213 | hsa-miR-570 | 0.3 | -1.07E+01 | 3.30E-19 | 2.78E-16 |
| 163 | hsa-miR-885-5p | 1.7 | 8.58E+00 | 3.88E-12 | 3.00E-09 |
| 100 | hsa-miR-1301 | 0.3 | -6.29E+00 | 7.60E-09 | 5.47E-06 |

Fig. 6D: HC vs. UC

| Seq ID NO: | mirna | fc | t | p | padj |
|---|---|---|---|---|---|
| 171 | hsa-miR-16 | 3.8 | 1.12E+01 | 3.10E-19 | 2.44E-16 |
| 173 | hsa-miR-34b | 2.1 | 1.43E+01 | 3.86E-24 | 3.22E-21 |
| 203 | hsa-miR-99b | 0.3 | -5.75E+00 | 1.02E-07 | 6.39E-05 |

Figure 7a

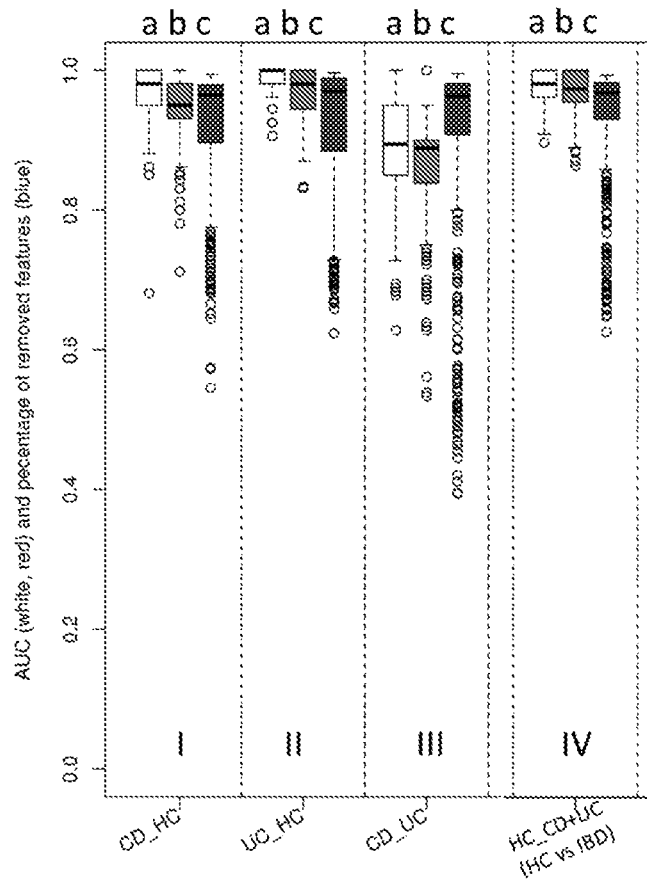

Figure 7b

| miRNA signature | miRNAs | AUC | Sens | Spec | BalAcc |
|---|---|---|---|---|---|
| I (HC vs CD) | hsa-miR-34b (SEQ ID NO: 173), hsa-miR-142-5p (SEQ ID NO: 167), hsa-miR-205 (SEQ ID NO: 174), hsa-miR-424 (SEQ ID NO: 200), hsa-miR-570 (SEQ ID NO: 213), hsa-miR-885-5p (SEQ ID NO: 163), hsa-miR-1301 (SEQ ID NO: 100) | 0.95 | 96 % | 100 % | 98% |
| II (HC vs UC) | hsa-miR-16 (SEQ ID NO: 171), hsa-miR-34b (SEQ ID NO: 173), hsa-miR-99b (SEQ ID NO: 203) | 0.98 | 100 % | 90% | 95% |
| III (CD vs UC) | hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) | 0.89 | 100 % | 83% | 92% |
| IV (HC vs CD+UC) | hsa-miR-98 (SEQ ID NO: 303), hsa-miR-199b-3p (SEQ ID NO: 52), hsa-miR-205 (SEQ ID NO: 174), hsa-miR-338-3p (SEQ ID NO: 253), hsa-miR-556-5p (SEQ ID NO: 15), hsa-miR-1225-5p (SEQ ID NO: 304), hsa-miR-1323 (SEQ ID NO: 64) | 0.97 | 100 % | 96% | 98% |

SEQUENCE LISTING

<160> NUMBER OF SEQ ID NOS: 304

<210> SEQ ID NO 1
<211> LENGTH: 19
<212> TYPE: RNA
<213> ORGANISM: Homo sapiens

<400> SEQUENCE: 1
accgugcaaa gguagcaua                                                    19

<210> SEQ ID NO 2
<211> LENGTH: 21
<212> TYPE: RNA
<213> ORGANISM: Homo sapiens

<400> SEQUENCE: 2
ggcuagcaac agcgcuuacc u                                                 21

<210> SEQ ID NO 3
<211> LENGTH: 22
<212> TYPE: RNA
<213> ORGANISM: Homo sapiens

<400> SEQUENCE: 3
aauugcacgg uauccaucug ua                                                22

<210> SEQ ID NO 4
<211> LENGTH: 21
<212> TYPE: RNA
<213> ORGANISM: Homo sapiens

<400> SEQUENCE: 4
acucuagcug ccaaaggcgc u                                                 21

<210> SEQ ID NO 5
<211> LENGTH: 22
<212> TYPE: RNA
<213> ORGANISM: Homo sapiens

<400> SEQUENCE: 5
cuauacgacc ugcugccuuu cu                                                22

<210> SEQ ID NO 6
<211> LENGTH: 22
<212> TYPE: RNA
<213> ORGANISM: Homo sapiens

<400> SEQUENCE: 6
cugaagcuca gagggcucug au                                                22

<210> SEQ ID NO 7
<211> LENGTH: 23
<212> TYPE: RNA
<213> ORGANISM: Homo sapiens

<400> SEQUENCE: 7
acuccauuug uuuugaugau gga                                               23

<210> SEQ ID NO 8
<211> LENGTH: 22
<212> TYPE: RNA
<213> ORGANISM: Homo sapiens

```
<400> SEQUENCE: 8
agucauugga ggguuugagc ag                                       22

<210> SEQ ID NO 9
<211> LENGTH: 22
<212> TYPE: RNA
<213> ORGANISM: Homo sapiens

<400> SEQUENCE: 9
aaaaguaauu gugguuuuug cc                                       22

<210> SEQ ID NO 10
<211> LENGTH: 20
<212> TYPE: RNA
<213> ORGANISM: Homo sapiens

<400> SEQUENCE: 10
cugcaaaggg aagcccuuuc                                          20

<210> SEQ ID NO 11
<211> LENGTH: 21
<212> TYPE: RNA
<213> ORGANISM: Homo sapiens

<400> SEQUENCE: 11
acagucugcu gagguuggag c                                        21

<210> SEQ ID NO 12
<211> LENGTH: 22
<212> TYPE: RNA
<213> ORGANISM: Homo sapiens

<400> SEQUENCE: 12
aaaaugguuc ccuuuagagu gu                                       22

<210> SEQ ID NO 13
<211> LENGTH: 17
<212> TYPE: RNA
<213> ORGANISM: Homo sapiens

<400> SEQUENCE: 13 guggggaga ggcuguc                                              17

<210> SEQ ID NO 14
<211> LENGTH: 24
<212> TYPE: RNA
<213> ORGANISM: Homo sapiens

<400> SEQUENCE: 14
ccagacagaa uucuaugcac uuuc                                     24

<210> SEQ ID NO 15
<211> LENGTH: 22
<212> TYPE: RNA
<213> ORGANISM: Homo sapiens

<400> SEQUENCE: 15
gaugagcuca uuguaauaug ag                                       22

<210> SEQ ID NO 16
<211> LENGTH: 22
<212> TYPE: RNA
<213> ORGANISM: Homo sapiens
```

<400> SEQUENCE: 16
acugauuucu uuggguguuc ag                                          22

<210> SEQ ID NO 17
<211> LENGTH: 18
<212> TYPE: RNA
<213> ORGANISM: Homo sapiens

<400> SEQUENCE: 17
ugcuuccuuu cagagggu                                                18

<210> SEQ ID NO 18
<211> LENGTH: 22
<212> TYPE: RNA
<213> ORGANISM: Homo sapiens

<400> SEQUENCE: 18
aagaugugga aaaauuggaa uc                                          22

<210> SEQ ID NO 19
<211> LENGTH: 22
<212> TYPE: RNA
<213> ORGANISM: Homo sapiens

<400> SEQUENCE: 19
ugcuaugcca acauauugcc au                                          22

<210> SEQ ID NO 20
<211> LENGTH: 20
<212> TYPE: RNA
<213> ORGANISM: Homo sapiens

<400> SEQUENCE: 20
auggagauag auauagaaau                                              20

<210> SEQ ID NO 21
<211> LENGTH: 22
<212> TYPE: RNA
<213> ORGANISM: Homo sapiens

<400> SEQUENCE: 21
acugcauuau gagcacuuaa ag                                          22

<210> SEQ ID NO 22
<211> LENGTH: 20
<212> TYPE: RNA
<213> ORGANISM: Homo sapiens

<400> SEQUENCE: 22
guugugucag uuuaucaaac                                              20

<210> SEQ ID NO 23
<211> LENGTH: 21
<212> TYPE: RNA
<213> ORGANISM: Homo sapiens

<400> SEQUENCE: 23
ugagcuaaau gugugcuggg a                                            21

<210> SEQ ID NO 24
<211> LENGTH: 23
<212> TYPE: RNA

```
<213> ORGANISM: Homo sapiens

<400> SEQUENCE: 24
uaagugcuuc cauguuuag uag                                              23

<210> SEQ ID NO 25
<211> LENGTH: 21
<212> TYPE: RNA
<213> ORGANISM: Homo sapiens

<400> SEQUENCE: 25
cacugugucc uuucugcgua g                                               21

<210> SEQ ID NO 26
<211> LENGTH: 21
<212> TYPE: RNA
<213> ORGANISM: Homo sapiens

<400> SEQUENCE: 26
agugaaugau ggguucugac c                                               21

<210> SEQ ID NO 27
<211> LENGTH: 22
<212> TYPE: RNA
<213> ORGANISM: Homo sapiens

<400> SEQUENCE: 27
auaagacgag caaaaagcuu gu                                              22

<210> SEQ ID NO 28
<211> LENGTH: 20
<212> TYPE: RNA
<213> ORGANISM: Homo sapiens

<400> SEQUENCE: 28
agaccauggg uucucauugu                                                 20

<210> SEQ ID NO 29
<211> LENGTH: 22
<212> TYPE: RNA
<213> ORGANISM: Homo sapiens

<400> SEQUENCE: 29
augcaccugg gcaaggauuc ug                                              22

<210> SEQ ID NO 30
<211> LENGTH: 22
<212> TYPE: RNA
<213> ORGANISM: Homo sapiens

<400> SEQUENCE: 30
uaacagucua cagccauggu cg                                              22

<210> SEQ ID NO 31
<211> LENGTH: 23
<212> TYPE: RNA
<213> ORGANISM: Homo sapiens

<400> SEQUENCE: 31
uacccuguag auccgaauuu gug                                             23

<210> SEQ ID NO 32
<211> LENGTH: 22
```

```
<212> TYPE: RNA
<213> ORGANISM: Homo sapiens

<400> SEQUENCE: 32
ugauugguac gucugugggu ag                                              22

<210> SEQ ID NO 33
<211> LENGTH: 18
<212> TYPE: RNA
<213> ORGANISM: Homo sapiens

<400> SEQUENCE: 33
cagggaggug aaugugau                                                   18

<210> SEQ ID NO 34
<211> LENGTH: 22
<212> TYPE: RNA
<213> ORGANISM: Homo sapiens

<400> SEQUENCE: 34
gugaaauguu uaggaccacu ag                                              22

<210> SEQ ID NO 35
<211> LENGTH: 21
<212> TYPE: RNA
<213> ORGANISM: Homo sapiens

<400> SEQUENCE: 35
uuaauaucgg acaaccauug u                                               21

<210> SEQ ID NO 36
<211> LENGTH: 22
<212> TYPE: RNA
<213> ORGANISM: Homo sapiens

<400> SEQUENCE: 36
agaaggaaau ugaauucauu ua                                              22

<210> SEQ ID NO 37
<211> LENGTH: 23
<212> TYPE: RNA
<213> ORGANISM: Homo sapiens

<400> SEQUENCE: 37
ugguuguagu ccgugcgaga aua                                             23

<210> SEQ ID NO 38
<211> LENGTH: 22
<212> TYPE: RNA
<213> ORGANISM: Homo sapiens

<400> SEQUENCE: 38
gcccaaaggu gaauuuuuug gg                                              22

<210> SEQ ID NO 39
<211> LENGTH: 21
<212> TYPE: RNA
<213> ORGANISM: Homo sapiens

<400> SEQUENCE: 39
uguucaugua gauguuuaag c                                               21

<210> SEQ ID NO 40
```

```
<211> LENGTH: 22
<212> TYPE: RNA
<213> ORGANISM: Homo sapiens

<400> SEQUENCE: 40
ggauuccugg aaauacuguu cu                                              22

<210> SEQ ID NO 41
<211> LENGTH: 21
<212> TYPE: RNA
<213> ORGANISM: Homo sapiens

<400> SEQUENCE: 41
aguuaggauu aggucgugga a                                               21

<210> SEQ ID NO 42
<211> LENGTH: 22
<212> TYPE: RNA
<213> ORGANISM: Homo sapiens

<400> SEQUENCE: 42
aacaucacag caagucugug cu                                              22

<210> SEQ ID NO 43
<211> LENGTH: 22
<212> TYPE: RNA
<213> ORGANISM: Homo sapiens

<400> SEQUENCE: 43
cacuggcucc uuucugggua ga                                              22

<210> SEQ ID NO 44
<211> LENGTH: 23
<212> TYPE: RNA
<213> ORGANISM: Homo sapiens

<400> SEQUENCE: 44
uagcaccauu ugaaaucagu guu                                             23

<210> SEQ ID NO 45
<211> LENGTH: 21
<212> TYPE: RNA
<213> ORGANISM: Homo sapiens

<400> SEQUENCE: 45
gguuuggucc uagccuuucu a                                               21

<210> SEQ ID NO 46
<211> LENGTH: 22
<212> TYPE: RNA
<213> ORGANISM: Homo sapiens

<400> SEQUENCE: 46
ugugacuggu ugaccagagg gg                                              22

<210> SEQ ID NO 47
<211> LENGTH: 19
<212> TYPE: RNA
<213> ORGANISM: Homo sapiens

<400> SEQUENCE: 47
ugucucugcu gggguuucu                                                  19
```

```
<210> SEQ ID NO 48
<211> LENGTH: 22
<212> TYPE: RNA
<213> ORGANISM: Homo sapiens

<400> SEQUENCE: 48
acucaaaaug ggggcgcuuu cc                                                22

<210> SEQ ID NO 49
<211> LENGTH: 22
<212> TYPE: RNA
<213> ORGANISM: Homo sapiens

<400> SEQUENCE: 49
gugaacgggc gccaucccga gg                                                22

<210> SEQ ID NO 50
<211> LENGTH: 23
<212> TYPE: RNA
<213> ORGANISM: Homo sapiens

<400> SEQUENCE: 50 agcuggbuguu gugaaucagg ccg                                              23

<210> SEQ ID NO 51
<211> LENGTH: 23
<212> TYPE: RNA
<213> ORGANISM: Homo sapiens

<400> SEQUENCE: 51
uggagacgcg gcccuguugg agu                                               23

<210> SEQ ID NO 52
<211> LENGTH: 22
<212> TYPE: RNA
<213> ORGANISM: Homo sapiens

<400> SEQUENCE: 52
acaguagucu gcacauuggu ua                                                22

<210> SEQ ID NO 53
<211> LENGTH: 24
<212> TYPE: RNA
<213> ORGANISM: Homo sapiens

<400> SEQUENCE: 53
agccuggaag cuggagccug cagu                                              24

<210> SEQ ID NO 54
<211> LENGTH: 23
<212> TYPE: RNA
<213> ORGANISM: Homo sapiens

<400> SEQUENCE: 54
aaggagcuua caaucuagcu ggg                                               23

<210> SEQ ID NO 55
<211> LENGTH: 22
<212> TYPE: RNA
<213> ORGANISM: Homo sapiens

<400> SEQUENCE: 55
ugaccgauuu cuccuggugu uc                                                22
```

```
<210> SEQ ID NO 56
<211> LENGTH: 22
<212> TYPE: RNA
<213> ORGANISM: Homo sapiens

<400> SEQUENCE: 56
uuuccggcuc gcugggugu gu                                              22

<210> SEQ ID NO 57
<211> LENGTH: 23
<212> TYPE: RNA
<213> ORGANISM: Homo sapiens

<400> SEQUENCE: 57
acuuaaacgu ggauguacuu gcu                                            23

<210> SEQ ID NO 58
<211> LENGTH: 19
<212> TYPE: RNA
<213> ORGANISM: Homo sapiens

<400> SEQUENCE: 58
agcugucuga aaaugucuu                                                 19

<210> SEQ ID NO 59
<211> LENGTH: 21
<212> TYPE: RNA
<213> ORGANISM: Homo sapiens

<400> SEQUENCE: 59
cuggauggcu ccuccauguc u                                              21

<210> SEQ ID NO 60
<211> LENGTH: 22
<212> TYPE: RNA
<213> ORGANISM: Homo sapiens

<400> SEQUENCE: 60
ggaggggucc cgcacuggga gg                                             22

<210> SEQ ID NO 61
<211> LENGTH: 22
<212> TYPE: RNA
<213> ORGANISM: Homo sapiens

<400> SEQUENCE: 61
aaguucuguu auacacucag gc                                             22

<210> SEQ ID NO 62
<211> LENGTH: 22
<212> TYPE: RNA
<213> ORGANISM: Homo sapiens

<400> SEQUENCE: 62
aguucuucag uggcaagcuu ua                                             22

<210> SEQ ID NO 63
<211> LENGTH: 17
<212> TYPE: RNA
<213> ORGANISM: Homo sapiens

<400> SEQUENCE: 63
ucccuguucg ggcgcca                                                   17
```

<210> SEQ ID NO 64
<211> LENGTH: 22
<212> TYPE: RNA
<213> ORGANISM: Homo sapiens

<400> SEQUENCE: 64
ucaaaacuga ggggcauuuu cu                                        22

<210> SEQ ID NO 65
<211> LENGTH: 22
<212> TYPE: RNA
<213> ORGANISM: Homo sapiens

<400> SEQUENCE: 65
uacgucaucg uugucaucgu ca                                        22

<210> SEQ ID NO 66
<211> LENGTH: 22
<212> TYPE: RNA
<213> ORGANISM: Homo sapiens

<400> SEQUENCE: 66
ccucccacac ccaaggcuug ca                                        22

<210> SEQ ID NO 67
<211> LENGTH: 21
<212> TYPE: RNA
<213> ORGANISM: Homo sapiens

<400> SEQUENCE: 67
uacucaaaaa gcugucaguc a                                         21

<210> SEQ ID NO 68
<211> LENGTH: 23
<212> TYPE: RNA
<213> ORGANISM: Homo sapiens

<400> SEQUENCE: 68
ucucacacag aaaucgcacc cgu                                       23

<210> SEQ ID NO 69
<211> LENGTH: 23
<212> TYPE: RNA
<213> ORGANISM: Homo sapiens

<400> SEQUENCE: 69
agcuucuuua cagugcugcc uug                                       23

<210> SEQ ID NO 70
<211> LENGTH: 21
<212> TYPE: RNA
<213> ORGANISM: Homo sapiens

<400> SEQUENCE: 70
agaccuggcc cagaccucag c                                         21

<210> SEQ ID NO 71
<211> LENGTH: 25
<212> TYPE: RNA
<213> ORGANISM: Homo sapiens

<400> SEQUENCE: 71
cccccacaac cgcgcuugac uagcu                                                      25

<210> SEQ ID NO 72
<211> LENGTH: 22
<212> TYPE: RNA
<213> ORGANISM: Homo sapiens

<400> SEQUENCE: 72
auaagacgaa caaaagguuu gu                                                         22

<210> SEQ ID NO 73
<211> LENGTH: 22
<212> TYPE: RNA
<213> ORGANISM: Homo sapiens

<400> SEQUENCE: 73
ucaggccagg cacaguggcu ca                                                         22

<210> SEQ ID NO 74
<211> LENGTH: 22
<212> TYPE: RNA
<213> ORGANISM: Homo sapiens

<400> SEQUENCE: 74
gauuagggug cuuagcuguu aa                                                         22

<210> SEQ ID NO 75
<211> LENGTH: 22
<212> TYPE: RNA
<213> ORGANISM: Homo sapiens

<400> SEQUENCE: 75
aaucaugugc agugccaaua ug                                                         22

<210> SEQ ID NO 76
<211> LENGTH: 22
<212> TYPE: RNA
<213> ORGANISM: Homo sapiens

<400> SEQUENCE: 76
uccuguacug agcugccccg ag                                                         22

<210> SEQ ID NO 77
<211> LENGTH: 22
<212> TYPE: RNA
<213> ORGANISM: Homo sapiens

<400> SEQUENCE: 77
cucccacugc uucacuugac ua                                                         22

<210> SEQ ID NO 78
<211> LENGTH: 22
<212> TYPE: RNA
<213> ORGANISM: Homo sapiens

<400> SEQUENCE: 78
cugguuucac augguggcuu ag                                                         22

<210> SEQ ID NO 79
<211> LENGTH: 19
<212> TYPE: RNA
<213> ORGANISM: Homo sapiens

<400> SEQUENCE: 79

-continued gaugaugcug cugaugcug                                                    19

<210> SEQ ID NO 80
<211> LENGTH: 20
<212> TYPE: RNA
<213> ORGANISM: Homo sapiens

<400> SEQUENCE: 80
uacaguauag augauguacu                                                   20

<210> SEQ ID NO 81
<211> LENGTH: 24
<212> TYPE: RNA
<213> ORGANISM: Homo sapiens

<400> SEQUENCE: 81
gaccuggaca uguuugugcc cagu                                              24

<210> SEQ ID NO 82
<211> LENGTH: 21
<212> TYPE: RNA
<213> ORGANISM: Homo sapiens

<400> SEQUENCE: 82
auauaugaug acuuagcuuu u                                                 21

<210> SEQ ID NO 83
<211> LENGTH: 22
<212> TYPE: RNA
<213> ORGANISM: Homo sapiens

<400> SEQUENCE: 83
gaggguuggg uggaggcucu cc                                                22

<210> SEQ ID NO 84
<211> LENGTH: 21
<212> TYPE: RNA
<213> ORGANISM: Homo sapiens

<400> SEQUENCE: 84
acggugcugg auguggccuu u                                                 21

<210> SEQ ID NO 85
<211> LENGTH: 21
<212> TYPE: RNA
<213> ORGANISM: Homo sapiens

<400> SEQUENCE: 85
gaaggcgcuu cccuuuggag u                                                 21

<210> SEQ ID NO 86
<211> LENGTH: 23
<212> TYPE: RNA
<213> ORGANISM: Homo sapiens

<400> SEQUENCE: 86
guccaguuuu cccaggaauc ccu                                               23

<210> SEQ ID NO 87
<211> LENGTH: 21
<212> TYPE: RNA
<213> ORGANISM: Homo sapiens

```
<400> SEQUENCE: 87
agagaagaag aucagccugc a                                              21

<210> SEQ ID NO 88
<211> LENGTH: 22
<212> TYPE: RNA
<213> ORGANISM: Homo sapiens

<400> SEQUENCE: 88
uaaugccccu aaaaauccuu au                                             22

<210> SEQ ID NO 89
<211> LENGTH: 22
<212> TYPE: RNA
<213> ORGANISM: Homo sapiens

<400> SEQUENCE: 89
ucccugagac ccuaacuugu ga                                             22

<210> SEQ ID NO 90
<211> LENGTH: 21
<212> TYPE: RNA
<213> ORGANISM: Homo sapiens

<400> SEQUENCE: 90
uccgguucuc agggcuccac c                                              21

<210> SEQ ID NO 91
<211> LENGTH: 22
<212> TYPE: RNA
<213> ORGANISM: Homo sapiens

<400> SEQUENCE: 91
aaaagcuggg uugagagggc ga                                             22

<210> SEQ ID NO 92
<211> LENGTH: 21
<212> TYPE: RNA
<213> ORGANISM: Homo sapiens

<400> SEQUENCE: 92
ccgucgccgc cacccgagcc g                                              21

<210> SEQ ID NO 93
<211> LENGTH: 18
<212> TYPE: RNA
<213> ORGANISM: Homo sapiens

<400> SEQUENCE: 93
gucccuguuc aggcgcca                                                  18

<210> SEQ ID NO 94
<211> LENGTH: 22
<212> TYPE: RNA
<213> ORGANISM: Homo sapiens

<400> SEQUENCE: 94
accaucgacc guugauugua cc                                             22

<210> SEQ ID NO 95
<211> LENGTH: 20
<212> TYPE: RNA
<213> ORGANISM: Homo sapiens
```

```
<400> SEQUENCE: 95
ccuccugccc uccuugcugu                                              20

<210> SEQ ID NO 96
<211> LENGTH: 23
<212> TYPE: RNA
<213> ORGANISM: Homo sapiens

<400> SEQUENCE: 96
aggcagugua guuagcugau ugc                                          23

<210> SEQ ID NO 97
<211> LENGTH: 23
<212> TYPE: RNA
<213> ORGANISM: Homo sapiens

<400> SEQUENCE: 97
ucggggauca ucaugucacg aga                                          23

<210> SEQ ID NO 98
<211> LENGTH: 22
<212> TYPE: RNA
<213> ORGANISM: Homo sapiens

<400> SEQUENCE: 98
aguauucugu accagggaag gu                                           22

<210> SEQ ID NO 99
<211> LENGTH: 27
<212> TYPE: RNA
<213> ORGANISM: Homo sapiens

<400> SEQUENCE: 99
cacuguaggu gauggugaga gugggca                                      27

<210> SEQ ID NO 100
<211> LENGTH: 24
<212> TYPE: RNA
<213> ORGANISM: Homo sapiens

<400> SEQUENCE: 100
uugcagcugc cugggaguga cuuc                                         24

<210> SEQ ID NO 101
<211> LENGTH: 27
<212> TYPE: RNA
<213> ORGANISM: Homo sapiens

<400> SEQUENCE: 101
auugaucauc gacacuucga acgcaau                                      27

<210> SEQ ID NO 102
<211> LENGTH: 22
<212> TYPE: RNA
<213> ORGANISM: Homo sapiens

<400> SEQUENCE: 102
aucacacaaa ggcaacuuuu gu                                           22

<210> SEQ ID NO 103
<211> LENGTH: 23
<212> TYPE: RNA
```

```
<213> ORGANISM: Homo sapiens

<400> SEQUENCE: 103
ccugcagcga cuugauggcu ucc                                        23

<210> SEQ ID NO 104
<211> LENGTH: 22
<212> TYPE: RNA
<213> ORGANISM: Homo sapiens

<400> SEQUENCE: 104
caguuaucac agugcugaug cu                                         22

<210> SEQ ID NO 105
<211> LENGTH: 25
<212> TYPE: RNA
<213> ORGANISM: Homo sapiens

<400> SEQUENCE: 105
aggcaccagc caggcauugc ucagc                                      25

<210> SEQ ID NO 106
<211> LENGTH: 22
<212> TYPE: RNA
<213> ORGANISM: Homo sapiens

<400> SEQUENCE: 106
cucuagaggg aagcgcuuuc ug                                         22

<210> SEQ ID NO 107
<211> LENGTH: 23
<212> TYPE: RNA
<213> ORGANISM: Homo sapiens

<400> SEQUENCE: 107
gcaaagcaca cggccugcag aga                                        23

<210> SEQ ID NO 108
<211> LENGTH: 21
<212> TYPE: RNA
<213> ORGANISM: Homo sapiens

<400> SEQUENCE: 108
aauauaacac agauggccug u                                          21

<210> SEQ ID NO 109
<211> LENGTH: 22
<212> TYPE: RNA
<213> ORGANISM: Homo sapiens

<400> SEQUENCE: 109
caggccauau ugugcugccu ca                                         22

<210> SEQ ID NO 110
<211> LENGTH: 21
<212> TYPE: RNA
<213> ORGANISM: Homo sapiens

<400> SEQUENCE: 110
uuaggccgca gaucugggug a                                          21

<210> SEQ ID NO 111
<211> LENGTH: 21
```

```
<212> TYPE: RNA
<213> ORGANISM: Homo sapiens

<400> SEQUENCE: 111
ugucuugcag gccgucaugc a                                              21

<210> SEQ ID NO 112
<211> LENGTH: 19
<212> TYPE: RNA
<213> ORGANISM: Homo sapiens

<400> SEQUENCE: 112
aggcacggug ucagcaggc                                                 19

<210> SEQ ID NO 113
<211> LENGTH: 19
<212> TYPE: RNA
<213> ORGANISM: Homo sapiens

<400> SEQUENCE: 113
gagccaguug gacaggagc                                                 19

<210> SEQ ID NO 114
<211> LENGTH: 23
<212> TYPE: RNA
<213> ORGANISM: Homo sapiens

<400> SEQUENCE: 114
cagugcaaug auauugucaa agc                                            23

<210> SEQ ID NO 115
<211> LENGTH: 20
<212> TYPE: RNA
<213> ORGANISM: Homo sapiens

<400> SEQUENCE: 115
cugcaaaggg aagcccuuuc                                                20

<210> SEQ ID NO 116
<211> LENGTH: 22
<212> TYPE: RNA
<213> ORGANISM: Homo sapiens

<400> SEQUENCE: 116
cucggcgcgg ggcgcgggcu cc                                             22

<210> SEQ ID NO 117
<211> LENGTH: 21
<212> TYPE: RNA
<213> ORGANISM: Homo sapiens

<400> SEQUENCE: 117
gcaguccaug ggcauauaca c                                              21

<210> SEQ ID NO 118
<211> LENGTH: 22
<212> TYPE: RNA
<213> ORGANISM: Homo sapiens

<400> SEQUENCE: 118
uauugcacau uacuaaguug ca                                             22

<210> SEQ ID NO 119
```

```
<211> LENGTH: 22
<212> TYPE: RNA
<213> ORGANISM: Homo sapiens

<400> SEQUENCE: 119
cucuagaggg aagcacuuuc ug                                              22

<210> SEQ ID NO 120
<211> LENGTH: 22
<212> TYPE: RNA
<213> ORGANISM: Homo sapiens

<400> SEQUENCE: 120
cucuagaggg aagcgcuuuc ug                                              22

<210> SEQ ID NO 121
<211> LENGTH: 23
<212> TYPE: RNA
<213> ORGANISM: Homo sapiens

<400> SEQUENCE: 121
aucaacagac auuaauuggg cgc                                             23

<210> SEQ ID NO 122
<211> LENGTH: 21
<212> TYPE: RNA
<213> ORGANISM: Homo sapiens

<400> SEQUENCE: 122
cuccagaggg aaguacuuuc u                                               21

<210> SEQ ID NO 123
<211> LENGTH: 23
<212> TYPE: RNA
<213> ORGANISM: Homo sapiens

<400> SEQUENCE: 123
gcagcagaga auaggacuac guc                                             23

<210> SEQ ID NO 124
<211> LENGTH: 21
<212> TYPE: RNA
<213> ORGANISM: Homo sapiens

<400> SEQUENCE: 124
cucccacaug caggguuugc a                                               21

<210> SEQ ID NO 125
<211> LENGTH: 21
<212> TYPE: RNA
<213> ORGANISM: Homo sapiens

<400> SEQUENCE: 125
uuggccacaa uggguuagaa c                                               21

<210> SEQ ID NO 126
<211> LENGTH: 22
<212> TYPE: RNA
<213> ORGANISM: Homo sapiens

<400> SEQUENCE: 126
ugcccugugg acucaguucu gg                                              22
```

```
<210> SEQ ID NO 127
<211> LENGTH: 22
<212> TYPE: RNA
<213> ORGANISM: Homo sapiens

<400> SEQUENCE: 127 ugugggcac agaaucugga cu                                              22

<210> SEQ ID NO 128
<211> LENGTH: 22
<212> TYPE: RNA
<213> ORGANISM: Homo sapiens

<400> SEQUENCE: 128
cugcgcaagc uacugccuug cu                                             22

<210> SEQ ID NO 129
<211> LENGTH: 22
<212> TYPE: RNA
<213> ORGANISM: Homo sapiens

<400> SEQUENCE: 129
ccucuagaug gaagcacugu cu                                             22

<210> SEQ ID NO 130
<211> LENGTH: 22
<212> TYPE: RNA
<213> ORGANISM: Homo sapiens

<400> SEQUENCE: 130
uuaucagaau cuccaggggu ac                                             22

<210> SEQ ID NO 131
<211> LENGTH: 22
<212> TYPE: RNA
<213> ORGANISM: Homo sapiens

<400> SEQUENCE: 131
cugugcgugu gacagcggcu ga                                             22

<210> SEQ ID NO 132
<211> LENGTH: 22
<212> TYPE: RNA
<213> ORGANISM: Homo sapiens

<400> SEQUENCE: 132
cucuagaggg aagcgcuuuc ug                                             22

<210> SEQ ID NO 133
<211> LENGTH: 21
<212> TYPE: RNA
<213> ORGANISM: Homo sapiens

<400> SEQUENCE: 133
augauccagg aaccugccuc u                                              21

<210> SEQ ID NO 134
<211> LENGTH: 21
<212> TYPE: RNA
<213> ORGANISM: Homo sapiens

<400> SEQUENCE: 134
aacauagagg aaauuccacg u                                              21
```

```
<210> SEQ ID NO 135
<211> LENGTH: 22
<212> TYPE: RNA
<213> ORGANISM: Homo sapiens

<400> SEQUENCE: 135
cuccugagcc auucugagcc uc                                              22

<210> SEQ ID NO 136
<211> LENGTH: 22
<212> TYPE: RNA
<213> ORGANISM: Homo sapiens

<400> SEQUENCE: 136
ugcggggcua gggcuaacag ca                                              22

<210> SEQ ID NO 137
<211> LENGTH: 22
<212> TYPE: RNA
<213> ORGANISM: Homo sapiens

<400> SEQUENCE: 137
uagcaaaaac ugcaguuacu uu                                              22

<210> SEQ ID NO 138
<211> LENGTH: 22
<212> TYPE: RNA
<213> ORGANISM: Homo sapiens

<400> SEQUENCE: 138
uacugcagac guggcaauca ug                                              22

<210> SEQ ID NO 139
<211> LENGTH: 22
<212> TYPE: RNA
<213> ORGANISM: Homo sapiens

<400> SEQUENCE: 139
gagcuuauuc auaaaagugc ag                                              22

<210> SEQ ID NO 140
<211> LENGTH: 22
<212> TYPE: RNA
<213> ORGANISM: Homo sapiens

<400> SEQUENCE: 140
cucuagaggg aagcgcuuuc ug                                              22

<210> SEQ ID NO 141
<211> LENGTH: 20
<212> TYPE: RNA
<213> ORGANISM: Homo sapiens

<400> SEQUENCE: 141
ccauggaucu ccaggugggu                                                 20

<210> SEQ ID NO 142
<211> LENGTH: 22
<212> TYPE: RNA
<213> ORGANISM: Homo sapiens

<400> SEQUENCE: 142
cucaucugca aagaaguaag ug                                              22
```

```
<210> SEQ ID NO 143
<211> LENGTH: 26
<212> TYPE: RNA
<213> ORGANISM: Homo sapiens

<400> SEQUENCE: 143
gugagggcau gcaggccugg augggg                                              26

<210> SEQ ID NO 144
<211> LENGTH: 23
<212> TYPE: RNA
<213> ORGANISM: Homo sapiens

<400> SEQUENCE: 144
ccucagggcu guagaacagg gcu                                                 23

<210> SEQ ID NO 145
<211> LENGTH: 22
<212> TYPE: RNA
<213> ORGANISM: Homo sapiens

<400> SEQUENCE: 145
ggugcagugc ugcaucucug gu                                                  22

<210> SEQ ID NO 146
<211> LENGTH: 19
<212> TYPE: RNA
<213> ORGANISM: Homo sapiens

<400> SEQUENCE: 146
aagcagcugc cucugaggc                                                      19

<210> SEQ ID NO 147
<211> LENGTH: 22
<212> TYPE: RNA
<213> ORGANISM: Homo sapiens

<400> SEQUENCE: 147
cugccaauuc cauaggucac ag                                                  22

<210> SEQ ID NO 148
<211> LENGTH: 21
<212> TYPE: RNA
<213> ORGANISM: Homo sapiens

<400> SEQUENCE: 148
ucacagugaa ccggucucuu u                                                   21

<210> SEQ ID NO 149
<211> LENGTH: 24
<212> TYPE: RNA
<213> ORGANISM: Homo sapiens

<400> SEQUENCE: 149
uucuccaaaa gaaagcacuu ucug                                                24

<210> SEQ ID NO 150
<211> LENGTH: 20
<212> TYPE: RNA
<213> ORGANISM: Homo sapiens

<400> SEQUENCE: 150
```

```
gugucugggc ggacagcugc                                              20

<210> SEQ ID NO 151
<211> LENGTH: 22
<212> TYPE: RNA
<213> ORGANISM: Homo sapiens

<400> SEQUENCE: 151
acaguagucu gcacauuggu ua                                           22

<210> SEQ ID NO 152
<211> LENGTH: 22
<212> TYPE: RNA
<213> ORGANISM: Homo sapiens

<400> SEQUENCE: 152
augcugacau auuuacuaga gg                                           22

<210> SEQ ID NO 153
<211> LENGTH: 20
<212> TYPE: RNA
<213> ORGANISM: Homo sapiens

<400> SEQUENCE: 153
ucugcagggu uugcuuugag                                              20

<210> SEQ ID NO 154
<211> LENGTH: 23
<212> TYPE: RNA
<213> ORGANISM: Homo sapiens

<400> SEQUENCE: 154
ugcaccaugg uugucugagc aug                                          23

<210> SEQ ID NO 155
<211> LENGTH: 22
<212> TYPE: RNA
<213> ORGANISM: Homo sapiens

<400> SEQUENCE: 155
gugacaucac auauacggca gc                                           22

<210> SEQ ID NO 156
<211> LENGTH: 21
<212> TYPE: RNA
<213> ORGANISM: Homo sapiens

<400> SEQUENCE: 156
uacugcagac aguggcaauc a                                            21

<210> SEQ ID NO 157
<211> LENGTH: 22
<212> TYPE: RNA
<213> ORGANISM: Homo sapiens

<400> SEQUENCE: 157
gggagccagg aaguauugau gu                                           22

<210> SEQ ID NO 158
<211> LENGTH: 23
<212> TYPE: RNA
<213> ORGANISM: Homo sapiens

<400> SEQUENCE: 158
```
uacugcauca ggaacugauu gga                                           23

<210> SEQ ID NO 159
<211> LENGTH: 22
<212> TYPE: RNA
<213> ORGANISM: Homo sapiens

<400> SEQUENCE: 159
ugugcgcagg gagaccucuc cc                                            22

<210> SEQ ID NO 160
<211> LENGTH: 22
<212> TYPE: RNA
<213> ORGANISM: Homo sapiens

<400> SEQUENCE: 160
aaaccguuac cauuacugag uu                                            22

<210> SEQ ID NO 161
<211> LENGTH: 22
<212> TYPE: RNA
<213> ORGANISM: Homo sapiens

<400> SEQUENCE: 161
uagcagcaca uaaugguuug ug                                            22

<210> SEQ ID NO 162
<211> LENGTH: 21
<212> TYPE: RNA
<213> ORGANISM: Homo sapiens

<400> SEQUENCE: 162
uggguuuacg uugggagaac u                                             21

<210> SEQ ID NO 163
<211> LENGTH: 22
<212> TYPE: RNA
<213> ORGANISM: Homo sapiens

<400> SEQUENCE: 163
uccauuacac uacccugccu cu                                            22

<210> SEQ ID NO 164
<211> LENGTH: 22
<212> TYPE: RNA
<213> ORGANISM: Homo sapiens

<400> SEQUENCE: 164
uuauaauaca accugauaag ug                                            22

<210> SEQ ID NO 165
<211> LENGTH: 22
<212> TYPE: RNA
<213> ORGANISM: Homo sapiens

<400> SEQUENCE: 165
cucuagaggg aagcgcuuuc ug                                            22

<210> SEQ ID NO 166
<211> LENGTH: 22
<212> TYPE: RNA
<213> ORGANISM: Homo sapiens

```
<400> SEQUENCE: 166
ugagguagua gauuguauag uu                                              22

<210> SEQ ID NO 167
<211> LENGTH: 21
<212> TYPE: RNA
<213> ORGANISM: Homo sapiens

<400> SEQUENCE: 167
cauaaaguag aaagcacuac u                                               21

<210> SEQ ID NO 168
<211> LENGTH: 22
<212> TYPE: RNA
<213> ORGANISM: Homo sapiens

<400> SEQUENCE: 168
aacacaccua uucaaggauu ca                                              22

<210> SEQ ID NO 169
<211> LENGTH: 21
<212> TYPE: RNA
<213> ORGANISM: Homo sapiens

<400> SEQUENCE: 169
gugggcgggg gcaggugugu g                                               21

<210> SEQ ID NO 170
<211> LENGTH: 21
<212> TYPE: RNA
<213> ORGANISM: Homo sapiens

<400> SEQUENCE: 170
uucaaguaau ucaggauagg u                                               21

<210> SEQ ID NO 171
<211> LENGTH: 22
<212> TYPE: RNA
<213> ORGANISM: Homo sapiens

<400> SEQUENCE: 171
uagcagcacg uaaauauugg cg                                              22

<210> SEQ ID NO 172
<211> LENGTH: 22
<212> TYPE: RNA
<213> ORGANISM: Homo sapiens

<400> SEQUENCE: 172
uguaaacauc cuugacugga ag                                              22

<210> SEQ ID NO 173
<211> LENGTH: 22
<212> TYPE: RNA
<213> ORGANISM: Homo sapiens

<400> SEQUENCE: 173
caaucacuaa cuccacugcc au                                              22

<210> SEQ ID NO 174
<211> LENGTH: 22
<212> TYPE: RNA
<213> ORGANISM: Homo sapiens
```

-continued

```
<400> SEQUENCE: 174
uccuucauuc caccggaguc ug                                              22

<210> SEQ ID NO 175
<211> LENGTH: 22
<212> TYPE: RNA
<213> ORGANISM: Homo sapiens

<400> SEQUENCE: 175
auaaagcuag auaaccgaaa gu                                              22

<210> SEQ ID NO 176
<211> LENGTH: 22
<212> TYPE: RNA
<213> ORGANISM: Homo sapiens

<400> SEQUENCE: 176
ugagguagua gguuguaugg uu                                              22

<210> SEQ ID NO 177
<211> LENGTH: 23
<212> TYPE: RNA
<213> ORGANISM: Homo sapiens

<400> SEQUENCE: 177
gcgaggaccc cucgggucu gac                                              23

<210> SEQ ID NO 178
<211> LENGTH: 18
<212> TYPE: RNA
<213> ORGANISM: Homo sapiens

<400> SEQUENCE: 178
uccagugccc uccucucc                                                   18

<210> SEQ ID NO 179
<211> LENGTH: 22
<212> TYPE: RNA
<213> ORGANISM: Homo sapiens

<400> SEQUENCE: 179
accuggcaua caauguagau uu                                              22

<210> SEQ ID NO 180
<211> LENGTH: 22
<212> TYPE: RNA
<213> ORGANISM: Homo sapiens

<400> SEQUENCE: 180
cauugcacuu gucucggucu ga                                              22

<210> SEQ ID NO 181
<211> LENGTH: 22
<212> TYPE: RNA
<213> ORGANISM: Homo sapiens

<400> SEQUENCE: 181
uagcuuauca gacugauguu ga                                              22

<210> SEQ ID NO 182
<211> LENGTH: 22
<212> TYPE: RNA
```

```
<213> ORGANISM: Homo sapiens

<400> SEQUENCE: 182
ugagguagga gguuguauag uu                                           22

<210> SEQ ID NO 183
<211> LENGTH: 23
<212> TYPE: RNA
<213> ORGANISM: Homo sapiens

<400> SEQUENCE: 183
uaaagugcuu auagugcagg uag                                          23

<210> SEQ ID NO 184
<211> LENGTH: 23
<212> TYPE: RNA
<213> ORGANISM: Homo sapiens

<400> SEQUENCE: 184
cucucaccac ugcccuccca cag                                          23

<210> SEQ ID NO 185
<211> LENGTH: 21
<212> TYPE: RNA
<213> ORGANISM: Homo sapiens

<400> SEQUENCE: 185
uacaguacug ugauaacuga a                                            21

<210> SEQ ID NO 186
<211> LENGTH: 22
<212> TYPE: RNA
<213> ORGANISM: Homo sapiens

<400> SEQUENCE: 186
ggauaucauc auauacugua ag                                           22

<210> SEQ ID NO 187
<211> LENGTH: 22
<212> TYPE: RNA
<213> ORGANISM: Homo sapiens

<400> SEQUENCE: 187
ucagcaaaca uuuauugugu gc                                           22

<210> SEQ ID NO 188
<211> LENGTH: 22
<212> TYPE: RNA
<213> ORGANISM: Homo sapiens

<400> SEQUENCE: 188
gguggcccgg ccgugccuga gg                                           22

<210> SEQ ID NO 189
<211> LENGTH: 22
<212> TYPE: RNA
<213> ORGANISM: Homo sapiens

<400> SEQUENCE: 189
ucguaccgug aguaauaaug cg                                           22

<210> SEQ ID NO 190
<211> LENGTH: 22
```

<212> TYPE: RNA
<213> ORGANISM: Homo sapiens

<400> SEQUENCE: 190
ugucaguuug ucaaauaccc ca                                        22

<210> SEQ ID NO 191
<211> LENGTH: 22
<212> TYPE: RNA
<213> ORGANISM: Homo sapiens

<400> SEQUENCE: 191
uguaaacauc cucgacugga ag                                        22

<210> SEQ ID NO 192
<211> LENGTH: 22
<212> TYPE: RNA
<213> ORGANISM: Homo sapiens

<400> SEQUENCE: 192
auauaauaca accugcuaag ug                                        22

<210> SEQ ID NO 193
<211> LENGTH: 21
<212> TYPE: RNA
<213> ORGANISM: Homo sapiens

<400> SEQUENCE: 193
uccugcgcgu cccagaugcc c                                         21

<210> SEQ ID NO 194
<211> LENGTH: 21
<212> TYPE: RNA
<213> ORGANISM: Homo sapiens

<400> SEQUENCE: 194
cugaccuaug aauugacagc c                                         21

<210> SEQ ID NO 195
<211> LENGTH: 23
<212> TYPE: RNA
<213> ORGANISM: Homo sapiens

<400> SEQUENCE: 195
caaagugcuu acagugcagg uag                                       23

<210> SEQ ID NO 196
<211> LENGTH: 18
<212> TYPE: RNA
<213> ORGANISM: Homo sapiens

<400> SEQUENCE: 196
cgggcguggu ggugggg                                              18

<210> SEQ ID NO 197
<211> LENGTH: 22
<212> TYPE: RNA
<213> ORGANISM: Homo sapiens

<400> SEQUENCE: 197
cacgcucaug cacacaccca ca                                        22

<210> SEQ ID NO 198

```
<211> LENGTH: 23
<212> TYPE: RNA
<213> ORGANISM: Homo sapiens

<400> SEQUENCE: 198
ugugcaaauc uaugcaaaac uga                                              23

<210> SEQ ID NO 199
<211> LENGTH: 22
<212> TYPE: RNA
<213> ORGANISM: Homo sapiens

<400> SEQUENCE: 199
ugagguagua guuuguacag uu                                               22

<210> SEQ ID NO 200
<211> LENGTH: 22
<212> TYPE: RNA
<213> ORGANISM: Homo sapiens

<400> SEQUENCE: 200
cagcagcaau ucauguuuug aa                                               22

<210> SEQ ID NO 201
<211> LENGTH: 23
<212> TYPE: RNA
<213> ORGANISM: Homo sapiens

<400> SEQUENCE: 201
uguaaacauc cuacacucuc agc                                              23

<210> SEQ ID NO 202
<211> LENGTH: 23
<212> TYPE: RNA
<213> ORGANISM: Homo sapiens

<400> SEQUENCE: 202
uauucauuua uccccagccu aca                                              23

<210> SEQ ID NO 203
<211> LENGTH: 22
<212> TYPE: RNA
<213> ORGANISM: Homo sapiens

<400> SEQUENCE: 203
cacccguaga accgaccuug cg                                               22

<210> SEQ ID NO 204
<211> LENGTH: 22
<212> TYPE: RNA
<213> ORGANISM: Homo sapiens

<400> SEQUENCE: 204
uagcaccauu ugaaaucggu ua                                               22

<210> SEQ ID NO 205
<211> LENGTH: 23
<212> TYPE: RNA
<213> ORGANISM: Homo sapiens

<400> SEQUENCE: 205
uagugcaaua uugcuuauag ggu                                              23
```

```
<210> SEQ ID NO 206
<211> LENGTH: 21
<212> TYPE: RNA
<213> ORGANISM: Homo sapiens

<400> SEQUENCE: 206
aucacauugc cagggauuac c                                      21

<210> SEQ ID NO 207
<211> LENGTH: 22
<212> TYPE: RNA
<213> ORGANISM: Homo sapiens

<400> SEQUENCE: 207
cuuggcaccu agcaagcacu ca                                     22

<210> SEQ ID NO 208
<211> LENGTH: 23
<212> TYPE: RNA
<213> ORGANISM: Homo sapiens

<400> SEQUENCE: 208
ugagugugug ugugugagug ugu                                    23

<210> SEQ ID NO 209
<211> LENGTH: 22
<212> TYPE: RNA
<213> ORGANISM: Homo sapiens

<400> SEQUENCE: 209
ugagguagua guuugugcug uu                                     22

<210> SEQ ID NO 210
<211> LENGTH: 21
<212> TYPE: RNA
<213> ORGANISM: Homo sapiens

<400> SEQUENCE: 210
ugcaggacca agaugagccc u                                      21

<210> SEQ ID NO 211
<211> LENGTH: 23
<212> TYPE: RNA
<213> ORGANISM: Homo sapiens

<400> SEQUENCE: 211
ugugcaaauc caugcaaaac uga                                    23

<210> SEQ ID NO 212
<211> LENGTH: 22
<212> TYPE: RNA
<213> ORGANISM: Homo sapiens

<400> SEQUENCE: 212
uucaccaccu ucuccaccca gc                                     22

<210> SEQ ID NO 213
<211> LENGTH: 22
<212> TYPE: RNA
<213> ORGANISM: Homo sapiens

<400> SEQUENCE: 213
cgaaaacagc aauuaccuuu gc                                     22
```

```
<210> SEQ ID NO 214
<211> LENGTH: 22
<212> TYPE: RNA
<213> ORGANISM: Homo sapiens

<400> SEQUENCE: 214
cucuagaggg aagcacuuuc uc                                                  22

<210> SEQ ID NO 215
<211> LENGTH: 22
<212> TYPE: RNA
<213> ORGANISM: Homo sapiens

<400> SEQUENCE: 215
cuggcccucu cugcccuucc gu                                                  22

<210> SEQ ID NO 216
<211> LENGTH: 22
<212> TYPE: RNA
<213> ORGANISM: Homo sapiens

<400> SEQUENCE: 216
uucaaguaau ccaggauagg cu                                                  22

<210> SEQ ID NO 217
<211> LENGTH: 21
<212> TYPE: RNA
<213> ORGANISM: Homo sapiens

<400> SEQUENCE: 217
gcgacccaua cuugguuuca g                                                   21

<210> SEQ ID NO 218
<211> LENGTH: 21
<212> TYPE: RNA
<213> ORGANISM: Homo sapiens

<400> SEQUENCE: 218
augaccuaug aauugacaga c                                                   21

<210> SEQ ID NO 219
<211> LENGTH: 22
<212> TYPE: RNA
<213> ORGANISM: Homo sapiens

<400> SEQUENCE: 219
ugagguagua gguugugugg uu                                                  22

<210> SEQ ID NO 220
<211> LENGTH: 22
<212> TYPE: RNA
<213> ORGANISM: Homo sapiens

<400> SEQUENCE: 220
ucggccugac cacccacccc ac                                                  22

<210> SEQ ID NO 221
<211> LENGTH: 23
<212> TYPE: RNA
<213> ORGANISM: Homo sapiens

<400> SEQUENCE: 221
caaagugcuc auagugcagg uag                                                 23
```

<210> SEQ ID NO 222
<211> LENGTH: 18
<212> TYPE: RNA
<213> ORGANISM: Homo sapiens

<400> SEQUENCE: 222
aucccaccuc ugccacca                                                 18

<210> SEQ ID NO 223
<211> LENGTH: 17
<212> TYPE: RNA
<213> ORGANISM: Homo sapiens

<400> SEQUENCE: 223
ucccaccgcu gccaccc                                                  17

<210> SEQ ID NO 224
<211> LENGTH: 23
<212> TYPE: RNA
<213> ORGANISM: Homo sapiens

<400> SEQUENCE: 224
aaaagugcuu acagugcagg uag                                           23

<210> SEQ ID NO 225
<211> LENGTH: 21
<212> TYPE: RNA
<213> ORGANISM: Homo sapiens

<400> SEQUENCE: 225
uucacagugg cuaaguucug c                                             21

<210> SEQ ID NO 226
<211> LENGTH: 21
<212> TYPE: RNA
<213> ORGANISM: Homo sapiens

<400> SEQUENCE: 226
cuguacaggc cacugccuug c                                             21

<210> SEQ ID NO 227
<211> LENGTH: 24
<212> TYPE: RNA
<213> ORGANISM: Homo sapiens

<400> SEQUENCE: 227
agcagaagca gggagguucu ccca                                          24

<210> SEQ ID NO 228
<211> LENGTH: 21
<212> TYPE: RNA
<213> ORGANISM: Homo sapiens

<400> SEQUENCE: 228
gaagugugcc guggugugguc u                                            21

<210> SEQ ID NO 229
<211> LENGTH: 21
<212> TYPE: RNA
<213> ORGANISM: Homo sapiens

<400> SEQUENCE: 229

| | |
|---|---|
| uggcagggag gcugggaggg g | 21 |

<210> SEQ ID NO 230
<211> LENGTH: 22
<212> TYPE: RNA
<213> ORGANISM: Homo sapiens

<400> SEQUENCE: 230

| | |
|---|---|
| cacuagauug ugagcuccug ga | 22 |

<210> SEQ ID NO 231
<211> LENGTH: 22
<212> TYPE: RNA
<213> ORGANISM: Homo sapiens

<400> SEQUENCE: 231

| | |
|---|---|
| ugagaacuga auuccauggg uu | 22 |

<210> SEQ ID NO 232
<211> LENGTH: 25
<212> TYPE: RNA
<213> ORGANISM: Homo sapiens

<400> SEQUENCE: 232

| | |
|---|---|
| gggcgacaaa gcaagacucu uucuu | 25 |

<210> SEQ ID NO 233
<211> LENGTH: 21
<212> TYPE: RNA
<213> ORGANISM: Homo sapiens

<400> SEQUENCE: 233

| | |
|---|---|
| uucacagugg cuaaguuccg c | 21 |

<210> SEQ ID NO 234
<211> LENGTH: 22
<212> TYPE: RNA
<213> ORGANISM: Homo sapiens

<400> SEQUENCE: 234

| | |
|---|---|
| uacccauugc auaucggagu ug | 22 |

<210> SEQ ID NO 235
<211> LENGTH: 22
<212> TYPE: RNA
<213> ORGANISM: Homo sapiens

<400> SEQUENCE: 235

| | |
|---|---|
| uuaugguuug ccugggacug ag | 22 |

<210> SEQ ID NO 236
<211> LENGTH: 22
<212> TYPE: RNA
<213> ORGANISM: Homo sapiens

<400> SEQUENCE: 236

| | |
|---|---|
| acuggacuua gggucagaag gc | 22 |

<210> SEQ ID NO 237
<211> LENGTH: 23
<212> TYPE: RNA
<213> ORGANISM: Homo sapiens

<400> SEQUENCE: 237
acuugggcac ugaaacaaug ucc                                              23

<210> SEQ ID NO 238
<211> LENGTH: 22
<212> TYPE: RNA
<213> ORGANISM: Homo sapiens

<400> SEQUENCE: 238
cagugcaaug uuaaaagggc au                                               22

<210> SEQ ID NO 239
<211> LENGTH: 22
<212> TYPE: RNA
<213> ORGANISM: Homo sapiens

<400> SEQUENCE: 239
cagccacaac uacccugcca cu                                               22

<210> SEQ ID NO 240
<211> LENGTH: 23
<212> TYPE: RNA
<213> ORGANISM: Homo sapiens

<400> SEQUENCE: 240
caaagugcug uucgugcagg uag                                              23

<210> SEQ ID NO 241
<211> LENGTH: 23
<212> TYPE: RNA
<213> ORGANISM: Homo sapiens

<400> SEQUENCE: 241
cagugcaaua guauugucaa agc                                              23

<210> SEQ ID NO 242
<211> LENGTH: 22
<212> TYPE: RNA
<213> ORGANISM: Homo sapiens

<400> SEQUENCE: 242
uguaacagca acuccaugug ga                                               22

<210> SEQ ID NO 243
<211> LENGTH: 23
<212> TYPE: RNA
<213> ORGANISM: Homo sapiens

<400> SEQUENCE: 243
agcagcauug uacagggcua uca                                              23

<210> SEQ ID NO 244
<211> LENGTH: 22
<212> TYPE: RNA
<213> ORGANISM: Homo sapiens

<400> SEQUENCE: 244
uagcaccauc ugaaaucggu ua                                               22

<210> SEQ ID NO 245
<211> LENGTH: 21
<212> TYPE: RNA
<213> ORGANISM: Homo sapiens -continued

<400> SEQUENCE: 245
ucacuccucu cucccgucu u                                          21

<210> SEQ ID NO 246
<211> LENGTH: 21
<212> TYPE: RNA
<213> ORGANISM: Homo sapiens

<400> SEQUENCE: 246
uccucuucuc ccuccuccca g                                         21

<210> SEQ ID NO 247
<211> LENGTH: 22
<212> TYPE: RNA
<213> ORGANISM: Homo sapiens

<400> SEQUENCE: 247
uguaaacauc cccgacugga ag                                        22

<210> SEQ ID NO 248
<211> LENGTH: 23
<212> TYPE: RNA
<213> ORGANISM: Homo sapiens

<400> SEQUENCE: 248
uggaagacua gugauuuugu ugu                                       23

<210> SEQ ID NO 249
<211> LENGTH: 21
<212> TYPE: RNA
<213> ORGANISM: Homo sapiens

<400> SEQUENCE: 249
agggagggac gggggcugug c                                         21

<210> SEQ ID NO 250
<211> LENGTH: 22
<212> TYPE: RNA
<213> ORGANISM: Homo sapiens

<400> SEQUENCE: 250 ucugccccu ccgcugcugc ca                                         22

<210> SEQ ID NO 251
<211> LENGTH: 22
<212> TYPE: RNA
<213> ORGANISM: Homo sapiens

<400> SEQUENCE: 251
ucagugcacu acagaacuuu gu                                        22

<210> SEQ ID NO 252
<211> LENGTH: 22
<212> TYPE: RNA
<213> ORGANISM: Homo sapiens

<400> SEQUENCE: 252
uauugcacuu gucccggccu gu                                        22

<210> SEQ ID NO 253
<211> LENGTH: 22
<212> TYPE: RNA
<213> ORGANISM: Homo sapiens -continued

```
<400> SEQUENCE: 253
uccagcauca gugauuuugu ug                                        22

<210> SEQ ID NO 254
<211> LENGTH: 22
<212> TYPE: RNA
<213> ORGANISM: Homo sapiens

<400> SEQUENCE: 254
ggcuacaaca caggacccgg gc                                        22

<210> SEQ ID NO 255
<211> LENGTH: 22
<212> TYPE: RNA
<213> ORGANISM: Homo sapiens

<400> SEQUENCE: 255
aaucauacag ggacauccag uu                                        22

<210> SEQ ID NO 256
<211> LENGTH: 22
<212> TYPE: RNA
<213> ORGANISM: Homo sapiens

<400> SEQUENCE: 256
aagcugccag uugaagaacu gu                                        22

<210> SEQ ID NO 257
<211> LENGTH: 22
<212> TYPE: RNA
<213> ORGANISM: Homo sapiens

<400> SEQUENCE: 257
acuccagccc cacagccuca gc                                        22

<210> SEQ ID NO 258
<211> LENGTH: 22
<212> TYPE: RNA
<213> ORGANISM: Homo sapiens

<400> SEQUENCE: 258
cggcaacaag aaacugccug ag                                        22

<210> SEQ ID NO 259
<211> LENGTH: 22
<212> TYPE: RNA
<213> ORGANISM: Homo sapiens

<400> SEQUENCE: 259
ugagguagua gguuguauag uu                                        22

<210> SEQ ID NO 260
<211> LENGTH: 23
<212> TYPE: RNA
<213> ORGANISM: Homo sapiens

<400> SEQUENCE: 260
uaaggugcau cuagugcaga uag                                       23

<210> SEQ ID NO 261
<211> LENGTH: 21
<212> TYPE: RNA
```

```
<213> ORGANISM: Homo sapiens

<400> SEQUENCE: 261
agcuacaucu ggcuacuggg u                                              21

<210> SEQ ID NO 262
<211> LENGTH: 23
<212> TYPE: RNA
<213> ORGANISM: Homo sapiens

<400> SEQUENCE: 262
uuuggcacua gcacauuuuu gcu                                            23

<210> SEQ ID NO 263
<211> LENGTH: 22
<212> TYPE: RNA
<213> ORGANISM: Homo sapiens

<400> SEQUENCE: 263
cggaugagca aagaaagugg uu                                             22

<210> SEQ ID NO 264
<211> LENGTH: 21
<212> TYPE: RNA
<213> ORGANISM: Homo sapiens

<400> SEQUENCE: 264
ugagaugaag cacuguagcu c                                              21

<210> SEQ ID NO 265
<211> LENGTH: 23
<212> TYPE: RNA
<213> ORGANISM: Homo sapiens

<400> SEQUENCE: 265
agcuacauug ucugcugggu uuc                                            23

<210> SEQ ID NO 266
<211> LENGTH: 20
<212> TYPE: RNA
<213> ORGANISM: Homo sapiens

<400> SEQUENCE: 266
ucacaccugc cucgccccc                                                 20

<210> SEQ ID NO 267
<211> LENGTH: 22
<212> TYPE: RNA
<213> ORGANISM: Homo sapiens

<400> SEQUENCE: 267
uugcauaguc acaaaaguga uc                                             22

<210> SEQ ID NO 268
<211> LENGTH: 17
<212> TYPE: RNA
<213> ORGANISM: Homo sapiens

<400> SEQUENCE: 268
ucgccuccuc cucuccc                                                   17

<210> SEQ ID NO 269
<211> LENGTH: 21
```

```
<212> TYPE: RNA
<213> ORGANISM: Homo sapiens

<400> SEQUENCE: 269
cagcagcaca cuggguuug u                                           21

<210> SEQ ID NO 270
<211> LENGTH: 21
<212> TYPE: RNA
<213> ORGANISM: Homo sapiens

<400> SEQUENCE: 270
cggcggggac ggcgauuggu c                                          21

<210> SEQ ID NO 271
<211> LENGTH: 22
<212> TYPE: RNA
<213> ORGANISM: Homo sapiens

<400> SEQUENCE: 271
caaagcgcuc cccuuuagag gu                                         22

<210> SEQ ID NO 272
<211> LENGTH: 24
<212> TYPE: RNA
<213> ORGANISM: Homo sapiens

<400> SEQUENCE: 272
aauccuugga accuaggugu gagu                                       24

<210> SEQ ID NO 273
<211> LENGTH: 21
<212> TYPE: RNA
<213> ORGANISM: Homo sapiens

<400> SEQUENCE: 273
aucacauugc cagggauuuc c                                          21

<210> SEQ ID NO 274
<211> LENGTH: 21
<212> TYPE: RNA
<213> ORGANISM: Homo sapiens

<400> SEQUENCE: 274
aucauagagg aaaauccacg u                                          21

<210> SEQ ID NO 275
<211> LENGTH: 21
<212> TYPE: RNA
<213> ORGANISM: Homo sapiens

<400> SEQUENCE: 275
aggaggcagc gcucucagga c                                          21

<210> SEQ ID NO 276
<211> LENGTH: 22
<212> TYPE: RNA
<213> ORGANISM: Homo sapiens

<400> SEQUENCE: 276
uuauaaagca augagacuga uu                                         22

<210> SEQ ID NO 277
```

```
<211> LENGTH: 22
<212> TYPE: RNA
<213> ORGANISM: Homo sapiens

<400> SEQUENCE: 277
uguaaacauc cuacacucag cu                                              22

<210> SEQ ID NO 278
<211> LENGTH: 22
<212> TYPE: RNA
<213> ORGANISM: Homo sapiens

<400> SEQUENCE: 278
caaccuggag gacuccaugc ug                                              22

<210> SEQ ID NO 279
<211> LENGTH: 21
<212> TYPE: RNA
<213> ORGANISM: Homo sapiens

<400> SEQUENCE: 279 agggguugcua ucugugauug a                                              21

<210> SEQ ID NO 280
<211> LENGTH: 22
<212> TYPE: RNA
<213> ORGANISM: Homo sapiens

<400> SEQUENCE: 280
aaccagcacc ccaacuuugg ac                                              22

<210> SEQ ID NO 281
<211> LENGTH: 21
<212> TYPE: RNA
<213> ORGANISM: Homo sapiens

<400> SEQUENCE: 281
cuagacugaa gcuccuugag g                                               21

<210> SEQ ID NO 282
<211> LENGTH: 24
<212> TYPE: RNA
<213> ORGANISM: Homo sapiens

<400> SEQUENCE: 282
ucccugagac ccuuuaaccu guga                                            24

<210> SEQ ID NO 283
<211> LENGTH: 21
<212> TYPE: RNA
<213> ORGANISM: Homo sapiens

<400> SEQUENCE: 283
acuggacuug gagucagaag g                                               21

<210> SEQ ID NO 284
<211> LENGTH: 23
<212> TYPE: RNA
<213> ORGANISM: Homo sapiens

<400> SEQUENCE: 284
ucaagagcaa uaacgaaaaa ugu                                             23
```

```
<210> SEQ ID NO 285
<211> LENGTH: 22
<212> TYPE: RNA
<213> ORGANISM: Homo sapiens

<400> SEQUENCE: 285
aaaucucugc aggcaaaugu ga                                              22

<210> SEQ ID NO 286
<211> LENGTH: 23
<212> TYPE: RNA
<213> ORGANISM: Homo sapiens

<400> SEQUENCE: 286
agcucggucu gaggccccuc agu                                             23

<210> SEQ ID NO 287
<211> LENGTH: 21
<212> TYPE: RNA
<213> ORGANISM: Homo sapiens

<400> SEQUENCE: 287
ccccaccucc ucucuccuca g                                               21

<210> SEQ ID NO 288
<211> LENGTH: 22
<212> TYPE: RNA
<213> ORGANISM: Homo sapiens

<400> SEQUENCE: 288
acgcccuucc ccccuucuu ca                                               22

<210> SEQ ID NO 289
<211> LENGTH: 22
<212> TYPE: RNA
<213> ORGANISM: Homo sapiens

<400> SEQUENCE: 289
uuuucaacuc uaaugggaga ga                                              22

<210> SEQ ID NO 290
<211> LENGTH: 23
<212> TYPE: RNA
<213> ORGANISM: Homo sapiens

<400> SEQUENCE: 290
uaaggugcau cuagugcagu uag                                             23

<210> SEQ ID NO 291
<211> LENGTH: 22
<212> TYPE: RNA
<213> ORGANISM: Homo sapiens

<400> SEQUENCE: 291
caugccuuga guguaggacc gu                                              22

<210> SEQ ID NO 292
<211> LENGTH: 23
<212> TYPE: RNA
<213> ORGANISM: Homo sapiens

<400> SEQUENCE: 292
uaauccuugc uaccugggug aga                                             23
```

```
<210> SEQ ID NO 293
<211> LENGTH: 25
<212> TYPE: RNA
<213> ORGANISM: Homo sapiens

<400> SEQUENCE: 293 aggggguggug uugggacagc uccgu                                          25

<210> SEQ ID NO 294
<211> LENGTH: 22
<212> TYPE: RNA
<213> ORGANISM: Homo sapiens

<400> SEQUENCE: 294
ucucccaacc cuuguaccag ug                                              22

<210> SEQ ID NO 295
<211> LENGTH: 19
<212> TYPE: RNA
<213> ORGANISM: Homo sapiens

<400> SEQUENCE: 295
aaaagcuggg uugagagga                                                  19

<210> SEQ ID NO 296
<211> LENGTH: 22
<212> TYPE: RNA
<213> ORGANISM: Homo sapiens

<400> SEQUENCE: 296
agagguagua gguugcauag uu                                              22

<210> SEQ ID NO 297
<211> LENGTH: 22
<212> TYPE: RNA
<213> ORGANISM: Homo sapiens

<400> SEQUENCE: 297
aucaugaugg gcuccucggu gu                                              22

<210> SEQ ID NO 298
<211> LENGTH: 22
<212> TYPE: RNA
<213> ORGANISM: Homo sapiens

<400> SEQUENCE: 298
ugucuuacuc ccucaggcac au                                              22

<210> SEQ ID NO 299
<211> LENGTH: 23
<212> TYPE: RNA
<213> ORGANISM: Homo sapiens

<400> SEQUENCE: 299
cccaguguuc agacuaccug uuc                                             23

<210> SEQ ID NO 300
<211> LENGTH: 21
<212> TYPE: RNA
<213> ORGANISM: Homo sapiens

<400> SEQUENCE: 300
aauauuauac agucaaccuc u                                               21
```

```
<210> SEQ ID NO 301
<211> LENGTH: 22
<212> TYPE: RNA
<213> ORGANISM: Homo sapiens

<400> SEQUENCE: 301
acccgucccg uucgucccg ga                                               22

<210> SEQ ID NO 302
<211> LENGTH: 22
<212> TYPE: RNA
<213> ORGANISM: Homo sapiens

<400> SEQUENCE: 302
ucaggcucag uccccucccg au                                              22

<210> SEQ ID NO 303
<211> LENGTH: 22
<212> TYPE: RNA
<213> ORGANISM: Homo sapiens

<400> SEQUENCE: 303
ugagguagua aguuguauug uu                                              22

<210> SEQ ID NO 304
<211> LENGTH: 22
<212> TYPE: RNA
<213> ORGANISM: Homo sapiens

<400> SEQUENCE: 304
guggguacgg cccagugggg gg                                              22
```

MIRNAS AS NON-INVASIVE BIOMARKERS FOR INFLAMMATORY BOWEL DISEASE

CROSS REFERENCE TO RELATED APPLICATIONS

This application is a U.S. National Phase of PCT/EP2015/066832, international filing date Jul. 23, 2015, which claims priority to European Application No. 14190596.8, filed Oct. 28, 2014 and European Application No. 15157101.5, filed Mar. 2, 2015, the disclosures of which are incorporated herein by reference for all purposes.

TECHNICAL FIELD OF THE INVENTION

The present invention relates to a method for diagnosis of Inflammatory Bowel Disease (IBD) based on the determination of expression profiles of miRNAs representative for diagnosis of IBD compared to a reference. In addition, the present invention relates to a kit for diagnosis of IBD comprising means for determining expression profiles of miRNAs representative for IBD.

BACKGROUND OF THE INVENTION

Today, biomarkers play a key role in early diagnosis, risk stratification, and therapeutic management of various diseases. While progress in biomarker research has accelerated over the last 5 years, the clinical translation of disease biomarkers as endpoints in disease management and as the foundation for diagnostic products still poses a challenge.

MicroRNAs (miRNAs) are a new class of biomarkers. They represent a group of small noncoding RNAs that regulate gene expression at the posttranslational level by degrading or blocking translation of messenger RNA (mRNA) targets. It has been found that miRNAs are expressed in a highly tissue-specific manner. Since recently it is known that miRNAs are not only present in tissues but also in body fluid samples, including blood. Nevertheless, the mechanism why miRNAs are found in blood, especially in blood cells or serum/plasma, or their function in these blood fractions is not understood yet.

Various miRNA biomarkers found in tissue material have been proposed to be correlated with certain diseases, e.g. cancer. Especially desirable are non-invasive biomarkers, that allow for quick, easy and cost-effective diagnosis/prognosis, eliminating the need for surgical intervention. Particularly, the potential role of miRNAs as non-invasive biomarkers for diagnosis of IBD (including differentiating Crohn's Disease from Ulcerative Colitis) has not been systematically evaluated yet. Accordingly, there is still a need for effective methods and kits for the non-invasive diagnosis of IBD, including differentiation between Crohn's Disease (CD) and Ulcerative Colitis (UC).

The inventors of the present invention assessed for the first time the expression of miRNAs on a whole-genome level in subjects with IBD as non-invasive biomarkers from blood cell samples. They surprisingly found that miRNAs are significantly dysregulated in blood, preferably in blood cell samples, more preferably in blood cell samples, even more preferably in blood cell samples comprising red blood cells, white blood cells or platelets of IBD subjects and thus, miRNAs are appropriated non-invasive biomarkers for diagnosis of IBD, including differentiating Crohn's Disease (CD) from Ulcerative Colitis (UC). The inventors of the present invention identified single miRNAs which predict diagnosis IBD (including differentiating CD from UC) with high specificity, sensitivity and accuracy. The inventors of the present invention also pursued a multiple biomarker strategy, combining at least two miRNA biomarkers to set (or signature) leading to added specificity, sensitivity, accuracy and predictive power in diagnosis of IBD (including differentiating CD from UC).

SUMMARY OF THE INVENTION

In a first aspect, the invention provides a method for diagnosing inflammatory bowel disease (namely for differentiating CD from UC), comprising the steps:
(i.) determining an expression profile of a set comprising at least two miRNAs representative for differentiating Healthy Control, Crohn's Disease and Ulcerative Colitis in a blood sample of a subject
(ii.) comparing said expression profile with a reference, wherein the comparison to the reference allows to determine if said subjects suffers from CD or from UC
wherein the nucleotide sequences of said miRNAs are selected from the group consisting of SEQ ID NO: 1 to 99.

In a second aspect, the invention provides the use of set of polynucleotides according to first aspect of the invention for diagnosing IBD (namely for differentiating CD from UC) in a subject In a third aspect, the invention provides a kit for diagnosing inflammatory bowel disease (namely for differentiating CD from UC) in a blood sample of a subject, comprising:
(i.) means for determining the expression profile of a set comprising at least two miRNAs selected from the group consisting of SEQ ID NO: 1 to 99 in a blood sample of a subject, and
(ii.) at least one reference
wherein the reference was obtained from expression profiles determined from CD and UC subjects from the same miRNAs in the same type of blood sample as the subject to be diagnosed.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences. The miRNAs regulate gene expression and are encoded by genes from whose DNA they are transcribed, but miRNAs are not translated into protein (i.e. miRNAs are non-coding RNAs). The terms "microRNA*" or "miRNA*" refer to miRNA molecules derived from the passenger strand upon processing. In the context of the present invention, the terms "miRNA" and "miRNA*" are interchangeable used. The miRBase (www.mirbase.org) is a well established repository and searchable database of published miRNA sequences and annotation. Because of the conservation of miRNAs among species, for example between humans and other mammals, e.g. animals such as mice, monkey or rat, the polynucleotide(s) of the invention may not only be suitable for detecting and/or quantifying a miRNA(s) of a specific species, e.g. a human miRNA, but may also be suitable for detecting the respective miRNA orthologue(s) in another species, e.g. in another mammal, e.g. in an animal such as mouse or rat.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group ($-CH_2-OH$), producing nucleotides, which are the molecular building blocks of DNA and RNA.

The term "polynucleotide", as used herein, means a molecule of at least 10 nucleotides and of not more than 70 nucleotides covalently linked together. Preferably, the polynucleotides of the present invention are molecules of 10 to 60 nucleotides or 15 to 50 nucleotides in length, more preferably of 17 to 35 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 99, 52, 53, 54, 55, 56, 57, 58, 59, 60, 61, 62, 63, 64, 65, 66, 67, 68, 69 or 70 nucleotides in length, not including optionally spacer elements and/or elongation elements. According to the present invention a polynucleotide is suitable for binding to, hybridizing to or detecting a (complementary) target, such as a miRNA or a target that is derived from a miRNA, such as a cDNA. Examples of polynucleotides suitable for binding to, hybridizing to or detecting a miRNA or a target derived from a miRNA, include—but are not limited to—probes on a solid substrate (e.g. microarray, beads), primers (RT-primers, PCR-primers).

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "whole blood sample", as used in the context of the present invention, refers to a blood sample originating from a subject containing all blood fractions, including both the cellular (red blood cells, white blood cells, platelets) and the extra-cellar blood fractions (serum, plasma). The whole blood sample may be derived by removing blood from a subject by conventional blood collecting techniques, but may also be provided by using previously isolated and/or stored blood samples. Preferably, the whole blood sample from a subject (e.g. human or animal) has a volume of between 0.1 and 20 ml, more preferably of between 0.5 and 15 ml, more preferably between 1 and 10 ml and most preferably between 2 and 7.5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 99, 12, 13, 14, 15, 16, 17, 18, 19, or 20 ml. Preferably the whole blood sample is collected by means of a blood collection tube, preferably it is collected in a PAXgene Blood RNA tube, in a Tempus Blood RNA tube, in an EDTA-tube (e.g. K2-EDTA Monovette tube), in a Na-citrate tube, Heparin-tube or in a ACD-tube (Acid citrate dextrose). Preferably, when the whole blood sample is collected, the RNA-fraction, especially the miRNA fraction, may be protected/guarded against degradation. For this purpose special collection tubes (e.g. PAXgene Blood RNA tubes from Preanalytix, Tempus Blood RNA tubes from Applied Biosystems) or additives (e.g. RNAlater from Ambion, RNAsin from Promega), that stabilize the RNA fraction and/or the miRNA fraction, may be employed.

The term "blood cell sample", as used in the context of the present invention, refers to a preparation of the whole blood sample, that (substantially) comprises or substantially comprises blood cells (red blood cells, white blood cells, platelets), more preferably the blood cell sample contains red blood cells, white blood cells and platelets, most preferably the blood cell sample consists of (a mixture of) red blood cells, white blood cells and platelets. Preferably, the blood cell sample does not contain miRNAs that originate from the extra-cellular fraction (e.g. plasma, serum) of whole blood or does contain miRNAs that originate from the extra-cellular fraction (e.g. plasma, serum) only in minor amounts in order that these do not or do not substantially contribute to the expression profile of the set of at least two miRNAs representative for IBD in a blood cell sample that is derived from a whole blood sample. Blood cell samples comprising red blood cells, white blood cells and/or platelets or blood cell samples containing red blood cells, white blood cells and platelets, most preferably the blood cell sample consists of (a mixture of) red blood cells, white blood cells and platelets are obtained from processing of whole blood samples collected in PAXgene Blood RNA Tubes, Tempus Blood RNA Tubes, EDTA-tubes (e.g. K2-EDTA Monovette tubes), Na-citrate tubes or Heparin-tubes, maintaining or substantially maintaining the initial cellular distribution (blood cell composition) of the whole blood sample. From the blood cell sample the total RNA (comprising the short RNA fraction including the miRNA fraction) is isolated and which is used for determining the expression profile of a set of miRNAs of a subject in said sample according to the present invention.

The term "total RNA" as used herein relates to the isolated RNA comprising the miRNA-fraction present in the respective blood cell sample, which is derived from a whole blood sample. Preferably, the total RNA according to the present invention contains the miRNA-fraction or contains a miRNA-enriched fraction of said total RNA. The total RNA (comprising the miRNA-fraction or miRNA-enriched fraction) is obtained by lysis (e.g. Trizol) of the blood cells in the blood cell sample, followed by RNA purification e.g. by phenol/chloroform extraction and/or separation based techniques (e.g. glass fiber filter column, silica-membrane column). Examples of kits for RNA isolation and purification include the miRNeasy Kits (Qiagen), PAXgene Blood miRNA Kit (Qiagen), mirVana PARIS Kit (Life Technologies), PARIS Kit (Life Technologies), Tempus Spin RNA Isolation Kit (Life Technologies).

The term "set comprising at least two miRNAs representative for differentiating Healthy Control, Crohn's Disease and Ulcerative Colitis", as used herein, refers to at least two fixed defined miRNAs comprised in a set which are known to be differential (regulated) between subjects suffering from Crohn's Disease, Ulcerative Colitis (IBD, diseased state) and Healthy Control subjects and thus allows not only to determine if a subjects suffers from IBD (namely differentiating if said subject is healthy (not suffering from IBD) or if said subject is suffering from IBD), but also allows to determine if a subjects suffers from CD or from UC. Said "set comprising at least two miRNAs representative for differentiating Healthy Control, Crohn's Disease and Ulcerative Colitis" are preferably selected from the group consisting of SEQ ID NO: 1 to 99 (FIG. 1), or from at least one set of miRNAs listed in FIG. 4. The set comprising at least two miRNAs representative for differentiating Healthy Control, Crohn's Disease and Ulcerative Colitis was developed by analyzing Healthy Controls, Crohn's Disease patients and Ulcerative Colitis patients (see FIG. 5), resulting in an optimal set of miRNA biomarkers for differentiating Crohn's Disease patients from Ulcerative Colitis, with also taking into account as an extra selection criterion the exclusion of False Positives (Healthy Control subjects, which are not suffering from either CD or UC). FIG. 6 depicts further miRNAs comprised in sets comprising at least two miRNAs representative for differentiating CD from UC (FIG. 6A), for differentiating Healthy Control (HC) from IBD (including CD and UC) in FIG. 6B, for differentiating Healthy Control (HC) from CD (FIG. 6C) and for differentiating Healthy Control (HC) from UC (FIG. 6D).

The term "expression profile" as used in the context of the present invention, represents the determination of the miRNA expression profile or a measure that correlates with the miRNA expression in a sample (e.g. in a blood cell sample derived from a whole blood sample). By determining the miRNA expression profile, each miRNA is represented by a numerical value. The higher the value of an individual miRNA, the higher is the expression level of said miRNA, or the lower the value of an individual miRNA, the lower is the expression level of said miRNA. The expression profile may be generated by any convenient means, e.g. nucleic acid hybridization (e.g. to a microarray), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX, Milipore Guava) and the like, that allow the analysis of miRNA expression profile in a subject and comparison between samples. The sample material measured by the aforementioned means are derived from a blood cell sample and may be a total RNA, labeled total RNA, amplified total RNA, cDNA, labeled cDNA, amplified cDNA, miRNA, labeled miRNA, amplified miRNA or any derivatives that may be generated from the aforementioned RNA/DNA species. The "expression profile", as used herein, relates to a collection of expression profiles of at least two miRNAs, preferably of least 2, 3, 4, 5, 6, 7, 8, 9, 10, 99, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 99 or more miRNAs.

The term "determining an expression profile in (from) a blood cell sample" as used herein, relates to the determination of the expression profile from the miRNAs present in said blood cell sample, therefore it is a measure that correlates with the miRNAs present in said blood cell sample. Herein, all steps or transformations required to bring the blood cell sample into a form which allows to record the expression profile by any convenient means (e.g. nucleic acid hybridisation, nucleic acid amplification, polymerase extension, mass spectroscopy, flow cytometry, sequencing) and which are known to the person skilled in the art, are included, e.g. cell-lysis, RNA-isolation, RNA-labeling, polymerase extension of RNA, ligation of RNA reverse-transcription into cDNA, amplification of the cDNA, labelling of cDNA, etc.

The term "diagnosis" as used in the context of the present invention refers to the process of determining a possible disease or disorder and therefore is a process attempting to define the (clinical) condition of a subject. The determination of the expression profile of at least two miRNAs according to the present invention correlates with the (clinical) condition of a subject. Preferably, the diagnosis comprises (i) determining the occurrence/presence of IBD, especially in an (very) early phase of the disease (ii) monitoring the course of IBD, (iii) staging of IBD, (iv) measuring the response of a patient with IBD to therapeutic intervention, and/or (v) segmentation of a subject suffering from IBD, (vi) differential diagnosis between CD and UC.

Nucleic acid hybridization may be performed using a microarray/biochip or in situ hybridization. For nucleic acid hybridization, for example, the polynucleotides (probes) according to the present invention with complementarity to the corresponding miRNAs to be detected are e.g. attached to a solid phase to generate a microarray/biochip (e.g. 99 polynucleotides (probes) which are complementary to the 99 miRNAs having SEQ ID NO: 1 to 99). Said microarray/biochip is then incubated with a sample containing miRNAs, isolated (e.g. extracted) from a blood cell sample derived from a whole blood sample from a subject, which may be labelled, e.g. fluorescently labelled, or unlabeled. Quantification of the expression level of the miRNAs may then be carried out e.g. by direct read out of a label or by additional manipulations, e.g. by use of a enzymatic reaction. Alternatively, the polynucleotides which are at least partially complementary (e.g. a set of chimeric polynucleotides with each a first stretch being complementary to a set of miRNA sequences and a second stretch complementary to capture probes bound to a solid surface (e.g. beads, Luminex beads)) to miRNAs having SEQ ID NO: 1 to 99 are contacted with said sample containing miRNAs in solution to hybridize. Afterwards, the hybridized duplexes are pulled down to the surface and successfully captured miRNAs are quantitatively determined (e.g. FlexmiR-assay, FlexmiR v2 detection assays from Luminex, Fireplex from Firefly Bioworks).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 10 miRNAs), whereas high-throughput RT-PCR technologies (e.g. OpenArray from Applied Biosystems, SmartPCR from Wafergen, Biomark System from Fluidigm) are also able to measure large sets (e.g. a set of 10, 20, 30, 50, 80, 100, 200 or more) to all known miRNAs in a high parallel fashion. RT-PCR is particularly suitable for detecting low abandoned miRNAs. The aforesaid real time polymerase chain reaction (RT-PCR) may include the following steps:
(i) extracting the total RNA from a blood cell sample derived from a whole blood sample of a subject, (ii) obtaining cDNA samples by RNA reverse transcription (RT) reaction using universal or miRNA-specific RT primers (e.g. stem-lopp RT primers); (iii) optionally amplifying the obtained cDNA (e.g. by PCR such as a specific target amplification (STA)), (iv) detecting the miRNA(s) level in the sample by means of (real time) quantification of the cDNA of step (ii) or (iii) e.g. by real time polymerase chain reaction wherein a fluorescent dye (e.g. SYBR Green) or a fluorescent probe (e.g. Taqman probe) probe are added. In Step (i) the isolation and/or extraction of RNA may be omitted in cases where the RT-PCR is conducted directly from the miRNA-containing sample. Kits for determining a miRNA expression profile by real time polymerase chain reaction (RT-PCR) are e.g. from Life Technologies, Applied Biosystems, Ambion, Roche, Qiagen, Invitrogen, SABiosciences, Exiqon.

The term "subject", as used in the context of the present invention, means a patient or individual suspected to be afflicted by IBD, e.g. suffering from CD or UC. The subject may be diagnosed to be afflicted by a specific form of IBD, hence afflicted by CD or UC. The patient may be diagnosed to be afflicted by IBD, i.e. diseased, or may be diagnosed to be not afflicted by IBD, i.e. healthy. The subject may further be diagnosed to develop IBD or a specific form of IBD (e.g. CD or UC) as the inventors of the present invention surprisingly found that miRNAs representative for IBD are already present in the blood cell sample derived from a whole blood sample an the early stage of IBD. It should be noted that a subject that is diagnosed as being healthy, i.e. not suffering from IBD or from a specific form of IBD, may possibly suffer from another disease not tested/known.

The term "inflammatory bowel disease (IBD)", as used herein refers to a group of inflammatory conditions of the colon and small intestine. The major types of IBD are Crohn's Disease (CD) and Ulcerative Colitis (UC). Inflammatory bowel diseases are considered autoimmune diseases, in which the body's own immune system attacks elements of the digestive system. Diagnosis is generally by assessment of inflammatory markers in stool followed by colonoscopy with biopsy of pathological lesions. Optimal treatment of inflammatory bowel disease depends on what form it consists of. For example, mesalazine is more useful in Ulcerative Colitis than in Crohn's Disease. Furthermore, antibiotics are generally not useful in UC, while they are effective in long-term in CD. UC is cured by removal of the colon, while such surgery is not helpful for CD patients, since the disease often returns following removal of affected part. So far it is still difficult to differentiate patients suffering from CD or UC. Therefore, for effective patient management it is of utmost importance to diagnose IBD with high performance (spec, sens), hence differentiate CD from UC in order to apply the most effective therapy to CD and UC patients. An overview of the miRNAs that are found to be significantly differentially regulated in blood samples, preferably in blood cell samples derived from a whole sample and that are suitable for diagnosis of IBD (namely for differentiating CD from UC) are provided in FIG. 1 (SEQ ID NO: 1-99) or FIG. 2, or sets of miRNAs for differentiating CD from UC as shown in FIG. 4. Further miRNAs for differentiating IBD from Healthy Controls are provided in FIG. 3. FIG. 6 depicts further miRNAs comprised in sets comprising at least two miRNAs representative for differentiating CD from UC (FIG. 6A), for differentiating Healthy Control (HC) from IBD (including CD and UC) in FIG. 6B, for differentiating Healthy Control (HC) from CD (FIG. 6C) and for differentiating Healthy Control (HC) from UC (FIG. 6D). An exemplarily approach to arrive at miRNA sets (signatures) that are useful in the diagnosis of IBD is summarized below:

Step 1: total RNA (comprising the miRNA fraction) is extracted from a blood sample, preferably from a blood cell samples derived from a whole sample using suitable kits and/or purification methods.

Step 2: From the respective samples the expression profile of at least two miRNAs, e.g. selected from the group consisting of SEQ ID NO: 1 to SEQ ID NO: 99, is measured using experimental techniques. These techniques include but are not limited to hybridisation based approaches, amplification methods (PCR, RT-PCR, qPCR), sequencing, next generation sequencing, flow cytometry and/or mass spectroscopy.

Step 3: In order to gather information on the diagnostic value and the redundancy of each of the single miRNA biomarkers, mathematical methods are applied. These methods include, but are not restricted to, basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in Step 3) together with other experimental parameters (e.g. signal intensity, fold change, miRNA origin) is used to estimate for each miRNA biomarker the diagnostic content and the analytical quality. Usually, however, this diagnostic value is too small to get a highly accurate diagnosis with accuracy rates, specificities and sensitivities beyond the 80-90% barrier. The diagnostic content of the single miRNAs representative for diagnosing IBD, namely differentiating CD from UC is exemplarily listed in FIG. 1 and further in FIG. 6A.

Step 5: In order to increase the performance for diagnosing of subjects suffering from IBD (namely for differentiating CD from UC), more than one biomarker may be employed. Thus statistical learning/machine learning/bioinformatics/computational approaches are applied for set selection in order to select at least two miRNA biomarker (e.g. comprising miRNAs SEQ ID NO: 1 to 99 or comprising at least one set of miRNAs listed in FIG. 4) to result in a tailored set (signature) of miRNA biomarkers suitable for diagnosis of IBD. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis of IBD (namely for differentiating CD from UC). To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning (Step 6) an algorithm or mathematical function for diagnosing IBD (namely for differentiating CD from UC) is obtained. This algorithm or mathematical function is applied to a miRNA expression profile for diagnosis of IBD (namely for differentiating CD from UC).

In a first aspect, the present invention relates to a method for diagnosing inflammatory bowel disease (namely for differentiating CD from UC), comprising the steps:
(i.) determining an expression profile of a set comprising at least two miRNAs representative for differentiating Healthy Control, Crohn's Disease and Ulcerative Colitis in a blood sample of a subject
(ii.) comparing said expression profile with a reference, wherein the comparison to the reference allows to determine if said subjects suffers from CD or from UC
wherein the nucleotide sequences of said miRNAs are selected from the group consisting of SEQ ID NO: 1 to 99.

The present invention relates to a method for differentiating CD from UC, comprising the steps:
(i.) determining an expression profile of a set comprising at least two miRNAs representative for differentiating CD from UC in a blood sample of a subject
(ii.) comparing said expression profile with a reference, wherein the comparison to the reference allows to determine if said subjects suffers from CD or from UC
wherein the nucleotide sequences of said miRNAs are selected from the group consisting of SEQ ID NO: 1 to 99.

The term microRNA expression profile as used herein represents the expression profile of a collection of at least 2 miRNAs comprised in the set, preferably at least, 3, 4, 5, 6, 7, 8, 9, 10, 1, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or 99 miRNAs, wherein the nucleic acid sequence of said miRNAs is selected from the group consisting of SEQ ID NO. 1 to SEQ ID NO: 99.

According to the present invention the expression profile is determined in a blood sample, preferably in a blood cell sample derived from a whole blood sample of a subject, preferably a human subject. Herein, the whole blood sample is collected from the subject by conventional blood draw techniques. Blood collection tubes suitable for collection of whole blood include EDTA- (e.g. K2-EDTA Monovette tube), Na-citrate-, ACD-, Heparin-, PAXgene Blood RNA-, Tempus Blood RNA-tubes. According to the present invention the collected whole blood sample, which intermediately may be stored before use, is processed to result in a blood cell sample of whole blood. This is achieved by separation of the blood cell fraction (the cellular fraction of whole blood) from the serum/plasma fraction (the extra-cellular fraction of whole blood). It is preferred, that the blood cell sample derived from the whole blood sample comprises red blood cells, white blood cells or platelets, it is more preferred that the blood cell sample derived from the whole blood sample comprises red blood cells, white blood cells and platelets, most preferably the blood cell sample derived from the whole blood sample consists of (a mixture of) red blood cells, white blood cells and platelets.

Preferably, the total RNA, including the miRNA fraction, or the miRNA-fraction is isolated from said blood cells present within said blood cell samples. Kits for isolation of total RNA including the miRNA fraction or kits for isolation of the miRNA-fraction are well known to those skilled in the art, e.g. miRNeasy-kit (Qiagen, Hilden, Germany), Paris-kit (Life Technologies, Weiterstadt, Germany). The miRNA-profile of said set comprising at least two miRNAs listed in FIG. 1 (SEQ ID NO. 1 to 99) or in FIG. 6A is then determined from the isolated RNA derived from the blood cells present within the blood cell sample of whole blood. Alternatively, the miRNA-profile of said set comprising at least two miRNAs listed in FIG. 1 (SEQ ID NO. 1 to SEQ ID NO: 99) or in FIG. 6A may be determined directly from the blood cell sample derived from the whole blood sample without the need for isolation of the RNA.

The determination of the expression profile may be by any convenient means for determining miRNAs or miRNA profiles. A variety of techniques are well known to those skilled in the art, e.g. nucleic acid hybridisation, nucleic acid amplification, sequencing, mass spectroscopy, flow cytometry based techniques or combinations thereof. According to the present invention the expression profile is determined from at least two miRNAs with nucleotide sequences selected from the group consisting of SEQ ID NO: 1 to SEQ ID NO: 99, which are listed in FIG. 1 or miRNAs listed in FIG. 6A.

Preferably the nucleic sequences of the at least two miRNAs comprised in the set when determining an expression profile in a blood cell sample derived from a whole blood sample have SEQ ID NO: 1 and SEQ ID NO: 2, the nucleic sequences of the at least two miRNAs comprised in the set have SEQ ID NO: 1 and SEQ ID NO: 3, the nucleic sequences of the at least two miRNAs comprised in the set have SEQ ID NO: 1 and SEQ ID NO: 4, the nucleic sequences of the at least two miRNAs comprised in the set have SEQ ID NO: 1 and SEQ ID NO: 5, the nucleic sequences of the at least two miRNAs comprised in the set have SEQ ID NO: 1 and SEQ ID NO: 6, the nucleic sequences of the at least two miRNAs comprised in the set have SEQ ID NO: 1 and SEQ ID NO: 7, the nucleic sequences of the at least two miRNAs comprised in the set have SEQ ID NO: 1 and SEQ ID NO: 8, the nucleic sequences of the at least two miRNAs comprised in the set have SEQ ID NO: 1 and SEQ ID NO: 9, the nucleic sequences of the at least two miRNAs comprised in the set have SEQ ID NO: 1 and SEQ ID NO: 10, the nucleic sequences of the at least two miRNAs comprised in the set have SEQ ID NO: 2 and SEQ ID NO: 3, the nucleic sequences of the at least two miRNAs comprised in the set have SEQ ID NO: 2 and SEQ ID NO: 4, the nucleic sequences of the at least two miRNAs comprised in the set have SEQ ID NO: 2 and SEQ ID NO: 5, the nucleic sequences of the at least two miRNAs comprised in the set have SEQ ID NO: 2 and SEQ ID NO: 6, the nucleic sequences of the at least two miRNAs comprised in the set have SEQ ID NO: 2 and SEQ ID NO: 7, the nucleic sequences of the at least two miRNAs comprised in the set have SEQ ID NO: 2 and SEQ ID NO: 8, the nucleic sequences of the at least two miRNAs comprised in the set have SEQ ID NO: 2 and SEQ ID NO: 9, the nucleic sequences of the at least two miRNAs comprised in the set have SEQ ID NO: 2 and SEQ ID NO: 10, the nucleic sequences of the at least two miRNAs comprised in the set have SEQ ID NO: 3 and SEQ ID NO: 4, the nucleic sequences of the at least two miRNAs comprised in the set have SEQ ID NO: 3 and SEQ ID NO: 5, the nucleic sequences of the at least two miRNAs comprised in the set have SEQ ID NO: 3 and SEQ ID NO: 6, the nucleic sequences of the at least two miRNAs comprised in the set have SEQ ID NO: 3 and SEQ ID NO: 7, the nucleic sequences of the at least two miRNAs comprised in the set have SEQ ID NO: 3 and SEQ ID NO: 8, the nucleic sequences of the at least two miRNAs comprised in the set have SEQ ID NO: 3 and SEQ ID NO: 9, the nucleic sequences of the at least two miRNAs comprised in the set have SEQ ID NO: 3 and SEQ ID NO: 10, the nucleic sequences of the at least two miRNAs comprised in the set have SEQ ID NO: 4 and SEQ ID NO: 5, the nucleic sequences of the at least two miRNAs comprised in the set have SEQ ID NO: 4 and SEQ ID NO: 6, the nucleic sequences of the at least two miRNAs comprised in the set have SEQ ID NO: 4 and SEQ ID NO: 7, the nucleic sequences of the at least two miRNAs comprised in the set have SEQ ID NO: 4 and SEQ ID NO: 8, the nucleic sequences of the at least two miRNAs comprised in the set have SEQ ID NO: 4 and SEQ ID NO: 9, the nucleic sequences of the at least two miRNAs comprised in the set have SEQ ID NO: 4 and SEQ ID NO: 10, the nucleic sequences of the at least two miRNAs comprised in the set have SEQ ID NO: 5 and SEQ ID NO: 6, the nucleic sequences of the at least two miRNAs comprised in the set have SEQ ID NO: 5 and SEQ ID NO: 7, the nucleic sequences of the at least two miRNAs comprised in the set have SEQ ID NO: 5 and SEQ ID NO: 8, the nucleic sequences of the at least two miRNAs comprised in the set have SEQ ID NO: 5 and SEQ ID NO: 9, the nucleic sequences of the at least two miRNAs comprised in the set have SEQ ID NO: 5 and SEQ ID NO: 10, the nucleic sequences of the at least two miRNAs comprised in the set have SEQ ID NO: 6 and SEQ ID NO: 7, the nucleic sequences of the at least two miRNAs comprised in the set have SEQ ID NO: 6 and SEQ ID NO: 8, the nucleic sequences of the at least two miRNAs comprised in the set have SEQ ID NO: 6 and SEQ ID NO: 9, the nucleic sequences of the at least two miRNAs comprised in the set have SEQ ID NO: 6 and SEQ ID NO: 10, the nucleic sequences of the at least two miRNAs comprised in the set have SEQ ID NO: 1 and SEQ ID NO: 8, the nucleic sequences of the at least two miRNAs comprised in the set have SEQ ID NO: 7 and SEQ ID NO: 9, the nucleic sequences of the at least two miRNAs comprised in the set have SEQ ID NO: 7 and SEQ ID NO: 10, the nucleic sequences of the at least two miRNAs comprised in the set have SEQ ID NO: 8 and SEQ ID NO: 9, the nucleic sequences of the at least two miRNAs comprised in the set have SEQ ID NO: 8 and SEQ ID NO: 10, or the nucleic sequences of the at least two miRNAs comprised in the set have SEQ ID NO: 9 and SEQ ID NO: 10.

The expression profile determined in step (i) above is then compared in step (ii) to a reference, wherein the reference is derived from the same set comprising at least two miRNAs, selected from the group consisting of SEQ ID NO: 1 to 99, representative for differentiating Healthy Control, Crohn's Disease and Ulcerative Colitis, which allows to differentiate between CD and UC (and further excludes that said subject is not suffering from IBD, namely not suffering from either CD or UC). The reference may be derived from a collection of expression profiles derived from at least two reference subjects or alternatively, the reference may represent a mathematical function, an algorithm, a classifier or a numeric threshold that was derived from a plurality of reference expression profiles derived from at least two reference subjects. It is preferred that the reference subjects are human subjects. It is preferred that the reference subjects belong to one of at least two groups of clinical conditions which are relevant for diagnosis of IBD, namely CD and UC, and which are to be diagnosed according to the method of the present invention. Preferably, the expression profile and the reference expression profile originate from the sample type of sample, preferably from a blood cell sample derived from a whole blood sample.

According to the present invention the comparison of the expression profile of a subject to the reference in step (ii) allows for the diagnosis of IBD, namely to differentiate CD from UC (to identify if said subject suffers from CD or from UC). Herein, the comparison will allow to diagnose that the subject belongs or that there is a statistical likelihood (or probability) that the subject belongs to one of at least two groups of clinical IBD conditions, namely CD or UC.

Optionally, the method of the present invention comprises a step (iii) for identifying a subject afflicted with IBD (CD or alternatively UC) for therapeutic intervention. Herein, subjects that are afflicted or diagnosed with IBD (CD or UC) are identified to be eligible for the respective therapeutic treatment, e.g. identified for application of first line treatment, identified for application of second line treatment, identified for change of treatment regime which is either suited for CD patient or alternatively for UC patients.

It is particularly preferred that the set of miRNAs comprises at least one set of miRNAs listed in FIG. 4. Thus, particularly preferred when determining the expression profile in a blood cell sample derived from a whole blood sample from a subject the set of miRNAs comprises a set of miRNAs with high diagnostic discrimination power for diagnosing IBD for differentiating CD from UC as listed in FIG. 4, selected from the group consisting of SCU-1 or a set of miRNAs comprising hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) which results in median AUC=0.89, 100% median sensitivity, 83% median specificity, 92% median balanced accuracy. Further particularly preferred, when determining the expression profile in a blood cell sample derived from a whole blood sample from a subject, the set of miRNAs comprises a set of miRNAs with high diagnostic discrimination power for diagnosing IBD listed in FIG. 4, such as SCU-1 (comprising SEQ ID NO: 1 to 99 resulting in 84.2% accuracy, in differentiating CD from UC) or a set of miRNAs comprising hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) which results in median AUC=0.89, 100% median sensitivity, 83% median specificity, 92% median balanced accuracy.

It is preferred that the expression profile is determined comprising the steps:
(a) Providing a whole blood sample of a subject suspected to suffer from CD or UC
(b) Deriving a blood cell sample from said whole blood sample
(c) Extracting the total RNA from said blood cell sample
(d) Determining the expression profile of a set comprising at least 2 miRNAs (selected from the group consisting of SEQ ID NO: 1 to 99) from the total RNA extracted Preferably, the blood cell sample is derived from a whole blood sample by separating the blood cells from the remaining parts of the whole blood sample, which may be achieved by centrifugation, wherein the blood cells (including red blood cells, white blood cells and platelets) form a pellet that may be harvested (see Example 1) while the supernatant containing the extra-cellular blood fraction is discarded. The person skilled in the art is aware of alternative methods to separate the blood cells from the remaining parts of the whole blood sample (e.g. size exclusion, size distribution, dielectrophoresis, positive or negative antibody selection etc.).

It is further preferred that the determining of the expression profile includes the reverse-transcription of the nucleotide sequence of the at least two miRNAs comprised in the set into cDNA (complementary DNA). Herein, the RNA-sequence is reverse-transcribed into DNA (e.g. by use of reverse-transcriptase) before the expression profile of said miRNAs is determined. Preferably, the nucleotide sequence of the at least two miRNAs comprised in the set is reverse-transcribed into cDNA when nucleic acid amplification (PCR, RT-PCR), sequencing (next generation sequencing, Sanger sequencing) or hybridisation based techniques are employed in the determination of the miRNA expression profile. Furthermore, it is preferred that the total RNA is transcribed into cDNA from which the expression profile is determined.

In a still further embodiment of the present invention, said subject is treated with medication suitable for treatment of CD- or UC-patients. Thus, as soon the subject is diagnosed to be afflicted with CD or UC, namely either CD or UC, said subject may receive the respective therapy (e.g. drug) for CD or UC. For example if said subject is diagnosed to be afflicted with CD, it may receive antibiotic treatment or alternatively a subject diagnosed with UC may receive Mesalazine or be subjected to surgery/colon removal.

In still a further embodiment the reference to which the expression profile of the subject to be diagnosed is compared was obtained from expression profiles determined from healthy control, CD and UC subjects from the same miRNAs in the same type of blood sample (namely a blood cell sample as detailed above) as the subject to be diagnosed.

It is further preferred that the set comprising at least two miRNAs according to the first aspect of the invention comprises 2, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 miRNAs selected from the group consisting of SEQ ID NO: 1 to 99. In a preferred embodiment, the set comprising at least two miRNAs according to the first aspect of the invention comprises all 99 miRNAs selected from the group consisting of SEQ ID NO: 1 to 99 (see SCU-1 in FIG. 4 or a set of miRNAs comprising hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) which results in median AUC=0.89, 100% median sensitivity, 83% median specificity, 92% median balanced accuracy). It is further preferred that the set comprising at least two miRNAs according to the first aspect of the invention further comprises miRNAs with nucleotide sequences selected from the group consisting of miRNAs listed in FIG. 2 or listed in FIG. 6A.

In a second aspect, the invention relates to the use of a set comprising polynucleotides for determining a set comprising at least 2 miRNAs in the method according to the first aspect of the invention. Hence, the present invention relates to the use of a set comprising polynucleotides for detecting a set comprising at least two miRNAs for diagnosing IBD (namely for differentiating CD from UC) in a blood cell sample derived from a whole blood sample from a subject, wherein the nucleotide sequences of the miRNAs comprised in the set are selected from the group consisting of SEQ ID NO: 1 to 99 or from FIG. 6A. It is understood that use of the set comprising polynucleotides of the second aspect of the invention includes and/or comprises the aspects detailed in the method according to the first aspect of the present invention.

It is preferred that the at least two miRNAs to be detected by the set comprising polynucleotides have a nucleotide sequences selected from the group consisting of SEQ ID NO: 1 to SEQ ID NO: 99 as listed in FIG. 1 or in FIG. 6A. For further particularly preferred sets of at least two miRNAs to be detected by the set comprising polynucleotides it is referred to the first aspect of the present invention and furthermore it is referred to FIG. 4. It is particularly preferred that the set of miRNAs comprises at least one set of miRNAs listed in FIG. 4, preferably selected from the group consisting of SCU-1 or a set of miRNAs comprising hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) which results in median AUC=0.89, 100% median sensitivity, 83% median specificity, 92% median balanced accuracy. For further particularly preferred sets of miRNAs with high diagnostic discrimination power for diagnosing IBD (namely for differentiating CD from UC) in a blood cell sample derived from whole blood it is referred to the first aspect of the present invention.

It is further preferred that according to the second aspect of the invention said polynucleotides comprised in the set
(i) are complementary to the miRNAs comprised in the set,
(ii) are complementary to cDNA-transcripts of the miRNAs comprised in the set,
(iii) are fragments of the polynucleotides comprised in the set according to (i), (ii), or
(iv) have at least 90% sequence identity to the polynucleotide sequences of the polynucleotides comprised in the set according to (i), (ii) or polynucleotide fragments comprised in the set according to (iii).

In a third aspect, the invention relates to a kit for diagnosing inflammatory bowel disease (namely for differentiating CD from UC) comprising.
(i.) means for determining the expression profile of a set comprising at least two miRNAs selected from the group consisting of SEQ ID NO: 1 to 99 in a blood sample of a subject, and
(ii.) at least one reference
wherein the reference was obtained from expression profiles determined from CD and UC subjects from the same miRNAs in the same type of blood sample as the subject to be diagnosed.

The invention relates to a kit for differentiating CD from UC comprising.
(i.) means for determining the expression profile of a set comprising at least two miRNAs selected from the group consisting of SEQ ID NO: 1 to 99 in a blood sample of a subject, and
(ii.) at least one reference
wherein the reference was obtained from expression profiles determined from CD and UC subjects from the same miRNAs in the same type of blood sample as the subject to be diagnosed.

It is understood that kit according to the third aspect of the invention includes and/or comprises the aspects detailed in the method according to the first aspect, the aspects detailed in the use of the set comprising polynucleotides according to the second aspect of the present invention. Preferably the expression profile for diagnosing inflammatory bowel disease (namely for differentiating CD from UC) is determined in a blood sample, preferably in a blood cell sample derived from a whole blood sample of a subject, preferably a human subject. It is preferred, that the blood cell sample derived from the whole blood sample comprises red blood cells, white blood cells or platelets, it is more preferred that the blood cell sample derived from the whole blood sample comprises red blood cells, white blood cells and platelets, most preferably the blood cell sample derived from the whole blood sample consists of (a mixture of) red blood cells, white blood cells and platelets.

It is preferred that the means of (i) are means for determining an expression profile of a set comprising at least two miRNAs representative for IBD, namely for differentiating CD from UC in a blood cell sample derived from a whole blood sample of a subject, wherein the nucleotide sequences of the miRNAs comprised in the set are selected from the group consisting of SEQ ID NO: 1 to 99. Preferably, said means for determining the expression profile comprise:
(i.) a set of at least two polynucleotides for determining a set comprising at least two miRNAs selected from the group consisting of SEQ ID NO: 1 to 99 in a blood sample of a subject, and
(ii.) a microarray, a RT-PCT system, a PCR-system, a flow cytometer, a bead-based multiplex system or a next generation sequencing system.

The kit comprises at least one reference according to the present invention as outlined in the first aspect of the present invention. In a preferred embodiment, the reference may be contained in the data carrier of the kit. In a further preferred embodiment the reference may be a reference sample and/or a reference standard that is included in the kit and which is employed when performing the kit, e.g. in the determining of the expression profile.

Optionally, the kit comprises a data carrier. Preferably the data carrier is an electronic or a non-electronic data carrier, more preferably it is an electronic data carrier, such as a storage medium. The kit optionally comprises a data carrier, which optionally comprises the reference and/or an instruction on how to apply the expression profile and the reference in the diagnosis of inflammatory bowel disease, namely for differentiating CD from UC. This instruction on how to apply the expression profile and the reference may include instructions for the doctor and/or the diagnostic laboratory that are involved in the diagnosing of IBD, namely involved in the diagnosis for differentiating CD from UC. It is preferred that the data carrier further comprises tools for analysis and evaluation of the determined expression profile (s). These tools may be any tools to assist the doctor and/or the diagnostic laboratory in the diagnosing of IBD, namely involved in the diagnosis for differentiating CD from UC. It is preferred that the instruction comprised is an algorithm or a software. Preferably, these tools are software-tools that assist in analysis of the determined expression profile(s) and/or assist in the subsequently diagnosis. The tools for analysis and evaluation may include a reference according to the present invention.

The kit optionally comprises a whole blood collection tube, which is preferably selected from group consisting of EDTA-, Na-citrate-, ACD-, Heparin-, PAXgene Blood RNA-, Tempus Blood RNA-tubes and optionally contains an additive for stabilizing the RNA-fraction.

The kit optionally comprises means for deriving the blood cell sample from a whole blood sample. These means are preferably for separating and/or isolating of the respective blood cell sample (e.g. a blood cell sample comprising white blood cells, red blood cells or platelets, a blood cell sample comprising white blood cells, red blood cells and platelets, a platelet-preparation) from the remaining parts of the whole blood sample. These means may include reagents or consumables for isolating/separating the respective blood cell fraction(s) and/or suitable instrumentation (e.g. centrifuge, special collection tubes).

In still a further embodiment the present invention relates to a method for diagnosing inflammatory bowel disease, comprising the steps:
(i.) determining an expression profile of a set comprising at least two miRNAs representative for differentiating Healthy Control from IBD (including Crohn's Disease and Ulcerative Colitis) in a blood sample of a subject
(ii.) comparing said expression profile with a reference, wherein the comparison to the reference allows to determine if said subjects suffers from IBD or not from IBD wherein the nucleotide sequences of said miRNAs are selected from the group consisting of miRNAs listed in FIG. 3 or in FIG. 6B.

It is understood that the method according to this further aspect of the invention includes and/or comprises the aspects detailed in the method according to the first aspect, the aspects detailed in the use of the set comprising polynucleotides according to the second aspect and the kit according to the third aspect of the present invention. Preferably said blood sample is a blood cell sample, more preferably a blood cell sample comprising red blood cells, white blood cells or platelets, even more preferably is a blood cell sample comprising red blood cells, white blood cells and platelets, most preferably the blood cell sample consists of (a mixture of) red blood cells, white blood cells and platelets. Furthermore it is preferred that the expression profile is determined comprising the steps: (a) Providing a whole blood sample of a subject suspected to suffer from IBD (CD or UC), (b) Deriving a blood cell sample from said whole blood sample, (c) Extracting the total RNA from said blood cell sample, (d) Determining the expression profile of a set comprising at least 2 miRNAs from the total RNA extracted. It is further preferred that the total RNA is transcribed into cDNA from which the expression profile is determined. Optionally said subjects diagnosed to be afflicted by IBD (CD or UC) are treated with medication suitable for treatment of CD- or UC-patients. It is particularly preferred that the set of miRNAs comprises at least one set of miRNAs listed in FIG. 3 or FIG. 4. Thus, particularly preferred when determining the expression profile in a blood cell sample derived from a whole blood sample from a subject the set of miRNAs comprises a set of miRNAs with high diagnostic discrimination power for diagnosing IBD from not suffering from IBD (e.g. being Healthy Control) as listed in FIG. 4, selected from the group consisting of SHI-1. Further particularly preferred, when determining the expression profile in a blood cell sample derived from a whole blood sample from a subject, the set of miRNAs comprises a set of miRNAs with high diagnostic discrimination power for diagnosing IBD listed in FIG. 4, such as SHI-1 (comprising SEQ ID NO: 1 to 99 resulting in 93.0% accuracy, in differentiating Healthy Control from IBD; see FIG. 5).

Preferred sets of at least 2 miRNAs in said method, kit or polynucleotides for diagnosing inflammatory bowel disease, namely for differentiating CD from UC, comprises hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) which results in median AUC=0.89, 100% median sensitivity, 83% median specificity, 92% median balanced accuracy. Preferred sets of at least 2 miRNAs in said method, kit or polynucleotides for diagnosing inflammatory bowel disease, namely for differentiating Healthy control (HC) from IBD (including CD and UC), comprises hsa-miR-98 (SEQ ID NO: 303), hsa-miR-199b-3p (SEQ ID NO: 52), hsa-miR-205 (SEQ ID NO: 174), hsa-miR-338-3p (SEQ ID NO: 253), hsa-miR-556-5p (SEQ ID NO: 15), hsa-miR-1225-5p (SEQ ID NO: 304), hsa-miR-1323 (SEQ ID NO: 64) resulting in median AUC=0.97, 100% median sensitivity, 96% median specificity, 98% median balanced accuracy.

Preferred sets of at least 2 miRNAs in said method, kit or polynucleotides for diagnosing inflammatory bowel disease, namely for differentiating Healthy control (HC) from CD, comprises hsa-miR-34b (SEQ ID NO: 173), hsa-miR-142-5p (SEQ ID NO: 167), hsa-miR-205 (SEQ ID NO: 174), hsa-miR-424 (SEQ ID NO: 200), hsa-miR-570 (SEQ ID NO: 213), hsa-miR-885-5p (SEQ ID NO: 163), hsa-miR-1301 (SEQ ID NO: 100) which results in median AUC=0.95, 96% median sensitivity, 100% median specificity, 98% median balanced accuracy Preferred sets of at least 2 miRNAs in said method, kit or polynucleotides for diagnosing inflammatory bowel disease, namely for differentiating Healthy control (HC) from UC, comprises hsa-miR-16 (SEQ ID NO: 171), hsa-miR-34b (SEQ ID NO: 173), hsa-miR-99b (SEQ ID NO: 203) resulting in median AUC=0.98, 100% median sensitivity, 90% median specificity, 95% median balanced accuracy.

In summary, the present invention is composed of the following items:
1. Method for diagnosing inflammatory bowel disease (namely for differentiating CD from UC), comprising the steps:
   (i.) determining an expression profile of a set comprising at least two miRNAs representative for differentiating Healthy Control, Crohn's Disease and Ulcerative Colitis in a blood sample of a subject
   (ii.) comparing said expression profile with a reference, wherein the comparison to the reference allows to determine if said subjects suffers from CD or from UC
   wherein the nucleotide sequences of said miRNAs are selected from the group consisting of SEQ ID NO: 1 to 99.
2. The method according to item 1, wherein the blood sample is a blood cell sample.
3. The method according to any of the items 1 to 2, wherein the expression profile is determined comprising the steps:
   (a) Providing a whole blood sample of a subject suspected to suffer from CD or UC
   (b) Deriving a blood cell sample from said whole blood sample
   (c) Extracting the total RNA from said blood cell sample
   (d) Determining the expression profile of a set comprising at least 2 miRNAs from the total RNA extracted
4. The method according to any of the items 1 to 3, wherein the total RNA is transcribed into cDNA from which the expression profile is determined.
5. The method according to any of the items 1 to 4, wherein optionally said subject (that is identified to be afflicted with CD or UC) is treated with medication suitable for treatment of CD- or UC-patients.

6. The method according to any of the items 1 to 5, wherein the set comprising at least two miRNAs comprises at least one set of miRNAs listed in FIG. 4.

7. The method according to any of the items 1 to 6 wherein the set comprising at least two miRNAs further comprises miRNAs with nucleotide sequences selected from the group consisting of miRNAs listed in FIG. 3.

8. The method according to any of the item 1 to 7, wherein the reference was obtained from expression profiles determined from CD and UC subjects from the same miRNAs in the same type of blood sample, preferably from the same blood cell sample, as the subject to be diagnosed.

9. The use of a set comprising polynucleotides for determining a set comprising at least 2 miRNAs in the method according to any of the items 1 to 8.

10. The use of a set comprising polynucleotides of item 9, wherein
    (i) the polynucleotides comprised in the set are complementary to the miRNAs comprised in the set,
    (ii) the polynucleotides comprised in the set are complementary to cDNA-transcripts of the miRNAs comprised in the set,
    (iii) the polynucleotides comprised in the set are fragments of the polynucleotides comprised in the set according to (i), (ii), or
    (iv) the polynucleotides comprised in the set have at least 90% sequence identity to the polynucleotide sequences of the polynucleotides comprised in the set according to (i), (ii) or polynucleotide fragments comprised in the set according to (iii).

11. Kit for diagnosing inflammatory bowel disease (namely for differentiating CD from UC) in a blood sample of a subject, comprising
    (i.) means for determining the expression profile of a set comprising at least two miRNAs selected from the group consisting of SEQ ID NO: 1 to 99 in a blood sample of a subject, and
    (ii.) at least one reference
    wherein the reference was obtained from expression profiles determined from CD and UC subjects from the same miRNAs in the same type of blood sample as the subject to be diagnosed.

12. The kit according to item 11, wherein said means comprise:
    (a) a set of at least two polynucleotides for determining a set comprising at least two miRNAs selected from the group consisting of SEQ ID NO: 1 to 99 in a blood sample of a subject, and
    (b) a microarray, a RT-PCT system, a PCR-system, a flow cytometer, a bead-based multiplex system or a next generation sequencing system.

13. The kit, according to any of the items 11 to 12, wherein the blood sample is a blood cell sample.

14. The kit, according to any of the items 11 to 13, wherein the kit optionally comprises a data carrier, which optionally comprises the reference and/or an instruction on how to apply the expression profile and the reference in the diagnosis of inflammatory bowel disease.

15. The kit according to item 14, wherein the instruction is an algorithm or a software.

16. Method for diagnosing inflammatory bowel disease, comprising the steps:
    (i.) determining an expression profile of a set comprising at least two miRNAs representative for differentiating Healthy Control and inflammatory bowel disease (incl. CD and UC) in a blood sample of a subject
    (ii.) comparing said expression profile with a reference, wherein the comparison to the reference allows to determine if said subjects is healthy or suffers from IBD
    wherein the nucleotide sequences of said miRNAs are selected from the group consisting of miRNAs listed in FIG. 3 or FIG. 6B.

17. The method according to item 16, wherein the blood sample is a blood cell sample.

18. The method according to any of the items 16 to 17, wherein the expression profile is determined comprising the steps:
    (a) Providing a whole blood sample of a subject suspected to suffer from IBD
    (b) Deriving a blood cell sample from said whole blood sample
    (c) Extracting the total RNA from said blood cell sample
    (d) Determining the expression profile of a set comprising at least 2 miRNAs from the total RNA extracted 19. The method according to item 18, wherein the total RNA is transcribed into cDNA from which the expression profile is determined.

20. The method according to any of the items 16 to 19, wherein optionally said subject when diagnosed with IBD is treated with medication suitable for treatment of IBD-patients.

21. The method according to any of the item 16 to 20, wherein the reference was obtained from expression profiles determined from healthy control and IBD (incl. CD and UC) subjects from the same miRNAs in the same type of blood sample, preferably from the same blood cell sample, as the subject to be diagnosed.

22. The use of a set comprising polynucleotides for determining a set comprising at least 2 miRNAs in the method according to any of the items 16 to 21.

23. The use of a set comprising polynucleotides of item 22, wherein
    (i.) the polynucleotides comprised in the set are complementary to the miRNAs comprised in the set,
    (ii.) the polynucleotides comprised in the set are complementary to cDNA-transcripts of the miRNAs comprised in the set,
    (iii.) the polynucleotides comprised in the set are fragments of the polynucleotides comprised in the set according to (i), (ii), or
    (iv.) the polynucleotides comprised in the set have at least 90% sequence identity to the polynucleotide sequences of the polynucleotides comprised in the set according to (i), (ii) or polynucleotide fragments comprised in the set according to (iii).

24. Kit for diagnosing inflammatory bowel disease in a blood sample of a subject, comprising
    (i.) means for determining the expression profile of a set comprising at least two miRNAs selected from the group consisting of miRNAs miRNAs listed in FIG. 3 or FIG. 6B in a blood sample, preferably in a blood cell sample, of a subject, and
    (ii.) at least one reference
    wherein the reference was obtained from expression profiles determined from healthy control and IBD (CD and UC) subjects from the same miRNAs in the same type of blood sample, preferably from the same blood cell sample, as the subject to be diagnosed.

25. Method for diagnosing inflammatory bowel disease, comprising the steps:
   (i.) determining an expression profile of a set comprising at least two miRNAs representative for differentiating CD from UC in a blood sample of a subject
   (ii.) comparing said expression profile with a reference, wherein the comparison to the reference allows to determine if said subjects is suffering from CD or UC wherein the nucleotide sequences of said miRNAs are selected from the group consisting of miRNAs listed in FIG. 2 or FIG. 6A.

26. The method according to item 25, wherein the blood sample is a blood cell sample.

27. The method according to any of the items 25 to 26, wherein the expression profile is determined comprising the steps:
   (a) Providing a whole blood sample of a subject suspected to suffer from CD or UC
   (b) Deriving a blood cell sample from said whole blood sample
   (c) Extracting the total RNA from said blood cell sample
   (d) Determining the expression profile of a set comprising at least 2 miRNAs from the total RNA extracted 28. The method according to item 27, wherein the total RNA is transcribed into cDNA from which the expression profile is determined.

29. The method according to any of the items 25 to 28, wherein optionally said subject when diagnosed with CD is treated with medication suitable for treatment of CD-patients or alternatively, when said subject is diagnosed with UC said subject is treated with medication suitable for treatment of UC-patients.

30. The method according to any of the item 25 to 29, wherein the reference was obtained from expression profiles determined from CD and UC subjects from the same miRNAs in the same type of blood sample, preferably from the same blood cell sample, as the subject to be diagnosed.

31. The use of a set comprising polynucleotides for determining a set comprising at least 2 miRNAs in the method according to any of the items 25 to 30.

32. The use of a set comprising polynucleotides of item 31, wherein
   (i.) the polynucleotides comprised in the set are complementary to the miRNAs comprised in the set,
   (ii.) the polynucleotides comprised in the set are complementary to cDNA-transcripts of the miRNAs comprised in the set,
   (iii.) the polynucleotides comprised in the set are fragments of the polynucleotides comprised in the set according to (i), (ii), or
   (iv.) the polynucleotides comprised in the set have at least 90% sequence identity to the polynucleotide sequences of the polynucleotides comprised in the set according to (i), (ii) or polynucleotide fragments comprised in the set according to (iii).

33. Kit for diagnosing inflammatory bowel disease, namely differentiating between CD and UC, in a blood sample of a subject, comprising
   (i.) means for determining the expression profile of a set comprising at least two miRNAs selected from the group consisting of miRNAs miRNAs listed in FIG. 2 or FIG. 6A in a blood sample, preferably in a blood cell sample, of a subject, and
   (ii.) at least one reference
   wherein the reference was obtained from expression profiles determined from CD and UC subjects from the same miRNAs in the same type of blood sample, preferably from the same blood cell sample, as the subject to be diagnosed.

34. The method, use or kit according to items 1 to 33, wherein the blood cell sample derived from a blood sample consists of a mixture of red blood cells, white blood cells and platelets 35. The method, use or kit according to items 1 to 34, wherein the blood cell sample derived from a blood sample does not comprise the extra-cellular blood fraction, preferably substantially does not comprise the extra-cellular blood fraction or components thereof.

36. The method according to items 3, 18 or 27, wherein in step (b) the extra-cellular blood fraction is discarded.

BRIEF DESCRIPTION OF THE DRAWINGS

FIG. 1: Overview of the miRNAs determined in blood cell samples derived from whole blood samples collected in K2-EDTA Monovette tubes (Sarstedt), comprising red blood cells, white blood cells and platelets that are found to be significantly differentially expressed in subjects suffering from Crohn's Disease, in subjects suffering from Ulcerative Colitis and in healthy controls and that are suitable for diagnosis of IBD, namely suitable both for differentiating Healthy Controls from IBD (including Crohn's Disease, Ulcerative Colitis patients) and for differentiating Crohn's Disease patients from Ulcerative Colitis patients. Thus, when applying these miRNAs for differentiating CD from UC, these miRNAs were specifically selected to reduce the false positive rate, since the exclusion of being not-afflicted with IBD (CD or UC) was used as an extra selection criterion in the development of said miRNAs selected from the group consisting of SEQ ID NO: 1 to 99. Herein, the blood samples from IBD-patients (CD- and UD-patients) and healthy controls were drawn into in K2-EDTA Monovette tubes, the total RNA of the blood cells—comprising the miRNA-fraction of blood cells—was isolated by use of the miRNeasy kit (http://www.qiagen.com) and analyzed on dna-microarrays (febit biomed) representing miRBase version 12 (see Experimental Section). Experimental details: SEQ ID NO: Sequence identification number; miRNA: miRNA annotation according to miRBase version 12; median g1(CD)=median expression level of the Crohn's Disease patients; median g2 (UC)=median expression level of the Ulcerative Colitis patients; qmedian=ratio of median g1 (CD) and median g2 (UC); ttest_adjp=Benjamini-Hochberg-adjusted p-value calculated according to ttest; AUC=area under the curve statistics; limma_adjp=Benjamini-Hochberg-adjusted p-value calculated according to limma-test.

FIG. 2: Overview of the miRNAs determined in blood cell samples derived from whole blood samples collected in K2-EDTA Monovette tubes (Sarstedt), comprising red blood cells, white blood cells and platelets that are found to be significantly differentially regulated, in subjects suffering from Crohn's Disease when compared to Ulcerative Colitis. The blood samples from CD-patients and UC-patients were drawn into K2-EDTA Monovette tubes, the total RNA of the blood cells—comprising the miRNA-fraction of blood cells—was isolated by use of the miRNeasy kit (http://www.qiagen.com) and analyzed on dna-microarrays (febit biomed) representing miRBase version 12. Experimental details: SEQ ID NO: Sequence identification number; miRNA: miRNA annotation according to miRBase version 12; median g1(CD)=median expression level of the Crohn's Disease patients; median g2 (UC)=median expression level of the Ulcerative Colitis patients; qmedian=ratio of median g1 (CD) and median g2 (UC); ttest_adjp=Benjamini-Hochberg-adjusted p-value calculated according to ttest; AUC=area under the curve statistics; limma_adjp=Benjamini-Hochberg-adjusted p-value calculated according to limma-test.

FIG. 3: Overview of the miRNAs determined in blood cell samples derived from whole blood samples collected in K2-EDTA Monovette tubes (Sarstedt), comprising red blood cells, white blood cells and platelets that are found to be significantly differentially regulated, in subjects suffering from IBD (including CD and UC patients) when compared to healthy controls and that are suitable for diagnosis of IBD from Healthy Control. The blood samples from IBD-patients (including CD- and UC-patients) and Healthy Controls were drawn into K2-EDTA Monovette tubes, the total RNA of the blood cells—comprising the miRNA-fraction of blood cells—was isolated by use of the miRNeasy kit (http://www.qiagen.com) and analyzed on dna-microarrays (febit biomed) representing miRBase version 12. Experimental details: SEQ ID NO: Sequence identification number; miRNA: miRNA annotation according to miRBase version 12 median g1(HC)=median expression level of the Healthy Controls; median g2 (IBD)=median expression level of the IBD (including CD- and UC-patients) patients; qmedian=ratio of median g1 (HC) and median g2 (IBD); ttest_adjp=Benjamini-Hochberg-adjusted p-value calculated according to ttest; AUC=area under the curve statistics; limma_adjp=Benjamini-Hochberg-adjusted p-value calculated according to limma-test.

FIG. 4: Overview of preferred sets of miRNA-biomarkers: SCU-1 is suitable for diagnosing IBD, namely differentiating between CD and UC with 84.2% accuracy, while SHI-1 is suitable for diagnosing IBD, namely differentiating between Healthy Control and IBD (including CD and UC) with 93% accuracy in blood cell samples derived from whole blood samples collected in K2-EDTA Monovette tubes (Sarstedt), comprising red blood cells, white blood cells and platelets. Experimental details: Signature: SEQ ID NO: sequence identification number; miRNA: identifier of the miRNAs according to miRBase version 12; Acc: statistical accuracy in %; Spec: statistical specificity in %; Sens: statistical sensitivity in %; bal. Acc: statistical balanced accuracy in %.

FIG. 5: Classification Performance of the 99 miRNAs determined in blood cell samples derived from whole blood samples collected in K2-EDTA Monovette tubes (Sarstedt), comprising red blood cells, white blood cells and platelets that are found to be suitable both for differentiating Healthy Controls from IBD (including Crohn's Disease, Ulcerative Colitis patients) and for differentiating Crohn's Disease patients from Ulcerative Colitis patients. Herein, the set consisting of 99 miRNAs (SEQ ID NO: 1 to 99) allows to classify Healthy Control and IBD-patients (including CD- and UC-patients) with 93% accuracy, while CD-patients can be classified from UC-patients with 84.2% accuracy employing the very same set of miRNAs. 40 Healthy Controls, 40 CD-patients and 36 UC-patients were used for the study. Experimental details: TP/F=True Positive False, herein 10 subjects were correctly classified for IBD, but were not correctly attributed to CD or UC; TP/True=True Positive True, herein 64 subjects were correctly classified for IBD and additionally correctly attributed to the two IBD-subgroups CD and UC; TN=True Negative, herein 32 subjects were correctly classified for Healthy Control; FP=False Positive, herein 6 subjects were not correctly classified to be IBD; FN=False Negative, herein 2 subjects were not correctly classified to be Healthy Control.

FIG. 6: Overview of further miRNAs determined in blood cell samples derived from whole blood samples collected in K2-EDTA Monovette tubes (Sarstedt), comprising red blood cells, white blood cells and platelets that are found to be differentially regulated in subjects suffering from CD when compared to UC (FIG. 6A), in subjects suffering from IBD (including subject suffering from CD, UC) when compared to healthy controls (FIG. 6B), in subjects suffering from CD when compared to healthy controls (FIG. 6C), in subjects suffering from UC when compared to healthy controls (FIG. 6D) and that are suitable for said diagnosis. Herein fc=fold change, t=t-statistic, p=p-value, padj=p-value adjusted for multiple testing using Holm-correction.

FIG. 7a: Classifier performance measured by the area under the ROC curve (AUC) for differentiating (I) CD from healthy control, (II) UC from healthy control, (III) CD from UC and (IV) HC from IBD (incl. CD+UC). Herein the boxplots (a) depict classifier performance (employing linear standard SVM) using all 863 miRNAs measured, boxplots (b) depict classifier performance (employing an elastic SCAD SVM) using only a subset (set, signature) of miRNAs and boxplots (c) depict the percentage of miRNAs neglected (in (b)) for constructing the respective classification model.

FIG. 7b: The subset (set, signature) of miRNAs of FIG. 7a in (I) consists of hsa-miR-34b (SEQ ID NO: 173), hsa-miR-142-5p (SEQ ID NO: 167), hsa-miR-205 (SEQ ID NO: 174), hsa-miR-424 (SEQ ID NO: 200), hsa-miR-570 (SEQ ID NO: 213), hsa-miR-885-5p (SEQ ID NO: 163), hsa-miR-1301 (SEQ ID NO: 100) resulting in median AUC=0.95, 96% median sensitivity, 100% median specificity, 98% median balanced accuracy; the subset (set, signature) of miRNAs in (II) consists of hsa-miR-16 (SEQ ID NO: 171), hsa-miR-34b (SEQ ID NO: 173), hsa-miR-99b (SEQ ID NO: 203) resulting in median AUC=0.98, 100% median sensitivity, 90% median specificity, 95% median balanced accuracy; the subset (set, signature) of miRNAs in (III) consists of hsa-miR-34b (SEQ ID NO: 173), hsa-miR-377 (SEQ ID NO: 102), hsa-miR-484 (SEQ ID NO: 302), hsa-miR-574-5p (SEQ ID NO: 208), hsa-miR-656 (SEQ ID NO: 300), hsa-miR-744 (SEQ ID NO: 136), hsa-miR-1247 (SEQ ID NO: 301), hsa-miR-1908 (SEQ ID NO: 270) resulting in median AUC=0.89, 100% median sensitivity, 83% median specificity, 92% median balanced accuracy; the subset (set, signature) of miRNAs in (IV) consists of hsa-miR-98 (SEQ ID NO: 303), hsa-miR-199b-3p (SEQ ID NO: 52), hsa-miR-205 (SEQ ID NO: 174), hsa-miR-338-3p (SEQ ID NO: 253), hsa-miR-556-5p (SEQ ID NO: 15), hsa-miR-1225-5p (SEQ ID NO: 304), hsa-miR-1323 (SEQ ID NO: 64) resulting in median AUC=0.97, 100% median sensitivity, 96% median specificity, 98% median balanced accuracy.

EXAMPLES

The Examples are designed in order to further illustrate the present invention and serve a better understanding. They are not to be construed as limiting the scope of the invention in any way.

Example 1: Deriving Blood Cell Samples from Whole Blood Samples

Blood of IBD (Crohn's Disease, Ulcerative Colitis) patients and healthy controls was drawn in into K2-EDTA Monovette tubes (Sarstedt). For each blood donor 9 ml of peripheral whole blood was collected in K2-EDTA Monovette tubes. The blood cells preparations were derived/obtained from processing the whole blood samples collected in K2-EDTA Monovette tubes by centrifugation. Herein, the blood cells from 3 ml whole blood collected in K2-EDTA tubes were spun down by 10 min, 5000×g centrifugation. The blood cell pellet (the cellular blood fraction comprising red blood cells, white blood cells and platelets) was harvested for further processing, while the supernatant (including the extra-cellular blood fraction) was discarded. Total RNA, including the small RNA (miRNA-fraction) was extracted from the harvested blood cells using the miRNeasy Mini Kit (Qiagen GmbH, Hilden, Germany); for details see Example 2.

Example 2: Isolation of Total RNA Incl. microRNA

The isolation of total RNA, including the small RNA (miRNA-fraction) was performed by use of the miRNeasy Mini Kit (Qiagen GmbH, Hilden, Germany). Herein, the blood cell pellet (obtained as outlined in Example 1) was thoroughly resuspended in 700 µl QIAzol lysis reagent by pipetting up and down and immediately the suspension was transferred to a new 1.5 ml Eppendorf tube. Then 140 µl chloroform were added, vortexed thoroughly and incubated for 2-3 min at room temperature, followed by centrifugation at 12,000 g for 15 min at 4° C. Afterwards, the upper, aqueous phase was transferred to a new 2 ml tube with great care, without touching the other two phases. Then 1.5 volumes of 100% ethanol were added to the transferred aqueous phase and thoroughly mixing was done by pipetting. 700 µl of sample were then transferred into a column and centrifuged at 13,000 rpm for 15 sec at RT, discarding the flow-through. Afterwards 700 µl of Buffer RWT were added to each column, centrifuged again at 13,000 rpm for 15 sec at RT, discarding the flow-through. Then 500 µl Buffer RPE was added to the column and centrifuged at 13,000 rpm for 15 sec at RT, discarding the flow-through. Afterwards another 500 µl Buffer RPE was added to the column and centrifuged at 13,000 rpm for 2 min at RT, discarding the flow-through. Then the column was placed into a new 2 ml collection tube and centrifuged at 13,000 rpm for 1 min at RT to dry it. The column was transferred into a new 1.5 ml collection tube. For elution of the total RNA incl. microRNA 40 µl RNase-free water was pipetted onto the column and incubated for 1 min, centrifuged at 13.000 rpm at RT for 1 min.

Then the eluate was put back onto the same column, incubated for 1 min at RT and centrifuged again for 1 min.

The eluted total RNA incl. microRNA was quantified using the NanoDrop 1000 and stored at −20° C. before use in expression profiling experiments.

For quality control of the total RNA, 1 µl of total RNA was applied on Agilent's Bioanalyzer, selecting either Agilent's nano- or pico-RNA Chip depending on RNA concentration determined by NanoDrop measurement.

Example 3: Microarray-Based Determination of Expression Profiles

The total RNA-samples including the miRNA-fraction (obtained by protocol Example 2) were analyzed employing microarray hybridization on the Geniom Realtime Analyzer (febit biomed GmbH, Heidelberg, Germany) using the Geniom Biochip miRNA *Homo sapiens*. Each microfluidic microarray contains complementary dna-probes of 866 miRNAs and miRNA* (each represented by 7 replicates) as annotated in the Sanger miRBase 12.0. Sample labeling with biotine has been carried out by enzymatic on-chip labeling of miRNAs employing febit's MPEA-assay. Following hybridization for 16 hours at 42° C. the biochip was washed automatically and a program for signal enhancement was processed with the Geniom Realtime Analyzer. The resulting detection pictures were evaluated using the Geniom Wizard Software. For each array, the median signal intensity was extracted from the raw data file such that for each miRNA seven intensity values have been calculated corresponding to each replicate copy of miRBase on the array. Following background correction, the seven replicate intensity values of each miRNA were summarized by their median value. To normalize the data across different arrays, quantile normalization was applied and all further analyses were carried out using the normalized and background subtracted intensity values (FIG. 1: g1=CD, g2=UC; FIG. 2: g1=CD, g2=UC; FIG. 3: g1=Healthy Control, g2=IBD (CD+UC)). From median g1 and median g2 the Fold Change of the expression (=qmedian) was calculated as the ratio g1/g2.

Example 4: Statistical Analysis

After having verified the normal distribution of the measured data, a parametric t-test (unpaired, two-tailed) was carried out for each miRNA separately, to detect miRNAs that show a different behavior in different groups of blood donors. The resulting raw p-values were adjusted for multiple testing by Benjamini-Hochberg adjustment (=ttest_adj). Furthermore, we applied the limma-test for each miRNA separately and corrected according to Benjamini-Hochberg (=limma_adj). Additionally, we applied receiver operating characteristics and calculated the "Area under the Curve"-value (=AUC). The ttest-, limma-test- and AUC-values allow to judge on the statistical significance for each miRNA to be differential expressed between group 1 (g1 subjects) and group 2 (g2 subjects).

Example 5: Classification Performance of Predetermined Sets of miRNAs

In addition to the single biomarker analysis and network analysis, classification of samples using miRNA patterns was carried out using Support Vector Machines (SVM,) as implemented in the R e1071 package. In detail, different kernel (linear, polynomial, sigmoid, radial basis function) Support Vector Machines were evaluated, where the cost parameter was sampled from 0.01 to 10 in decimal powers. The measured miRNA profiles were classified using 100 repetitions of standard 10-fold cross-validation. As a subset selection technique we applied a filter approach based on selecting the miRNAs with SEQ ID NO: 1-99 and further subsets comprising of 2 or more miRNAs thereof. As result, the mean accuracy (=Acc), specificity (=Spec), and sensitivity (=Sens) were calculated for each subset size. To check for overtraining permutation tests were applied. Here the class labels were sampled randomly and classifications were carried out using the permuted class labels. All statistical analyzes were performed using R. FIG. 4 and FIG. 5 list preferred sets of miRNAs and the classification performance (accuracy, specificity, sensitivity, balance accuracy) of predefined sets of miRNAs. This translates to the accuracy, specificity, sensitivity and balanced accuracy that is obtained when the classifier comprising the sets of preferred miRNAs is applied to classification between the investigated 2 groups.

The invention claimed is:

1. A method for differentiating Crohn's Disease (CD) from Ulcerative Colitis (UC), comprising the steps of:
   (i) determining expression level of a miRNA having a nucleotide sequence of SEQ ID NO:1 in a blood sample of a subject;
   (ii) comparing said expression level from step (i) with a reference representing average level of the same miRNA in the same type of blood sample in CD patients and with a reference representing average level of the same miRNA in the same type of blood sample in UC patient; and
   (iii) detecting CD in a subject when the expression level from step (i) is less than the UC reference and treating the subject having CD by antibiotic administration, or detecting UC in a subject when the expression level from step (i) is greater than the CD reference and treating the subject having UC by Mesalazine administration or colon surgery/removal.

2. The method according to claim 1, wherein the blood sample is a blood cell sample.

3. The method according to claim 1, wherein the expression level is determined comprising the steps of:
   (a) providing a whole blood sample of a subject suspected to suffer from CD or UC;
   (b) deriving a blood cell sample from said whole blood sample;
   (c) extracting the total RNA from said blood cell sample; and
   (d) determining the expression level of the miRNA from the total RNA extracted.

4. The method according to claim 3, wherein the total RNA is transcribed into cDNA from which the expression level is determined.

5. The method according to claim 1, wherein in step (i) polynucleotide for determining the miRNA is used.

6. The method according to claim 5, wherein
   (i) the polynucleotide is complementary to the miRNA,
   (ii) the polynucleotide is complementary to cDNA-transcript of the miRNA,
   (iii) the polynucleotide is a fragment of the polynucleotide according to (i), (ii) (i) or (ii), or
   (iv) the polynucleotide has at least 90% sequence identity to the polynucleotide sequence of the polynucleotide according to (i) or (ii) or polynucleotide fragment according to (iii).

7. The method of claim 1, wherein expression level of one or more additional miRNA having a nucleotide sequence selected from the group consisting of SEQ ID NO: 2 to SEQ ID NO: 99 is determined in a blood sample of a subject.

8. The method of claim 1, wherein the expression level of the miRNAs according to SEQ ID NO: 1 to SEQ ID NO: 99 is determined in a blood sample of a subject.

9. The method of claim 1, wherein the expression level of one or more additional miRNA having a nucleotide sequence selected from the group consisting of SEQ ID Nos: 2, 3, 4, 6, 10, 13, 15, 19, 100 to 163 is determined in a blood sample of a subject.

* * * * *